(12) United States Patent
Alshaer et al.

(10) Patent No.: US 10,278,639 B2
(45) Date of Patent: May 7, 2019

(54) METHOD AND SYSTEM FOR SLEEP DETECTION

(71) Applicant: UNIVERSITY HEALTH NETWORK, Toronto (CA)

(72) Inventors: Hisham Alshaer, Mississauga (CA); T. Douglas Bradley, Toronto (CA)

(73) Assignee: University Health Network, Toronto (CA)

( * ) Notice: Subject to any disclaimer, the term of this patent is extended or adjusted under 35 U.S.C. 154(b) by 809 days.

(21) Appl. No.: 14/694,198

(22) Filed: Apr. 23, 2015

(65) Prior Publication Data

US 2015/0313535 A1    Nov. 5, 2015

Related U.S. Application Data

(60) Provisional application No. 62/005,096, filed on May 30, 2014, provisional application No. 61/987,941, filed on May 2, 2014.

(51) Int. Cl.
*A61B 5/08* (2006.01)
*A61B 5/00* (2006.01)
*A61B 7/00* (2006.01)

(52) U.S. Cl.
CPC .......... *A61B 5/4812* (2013.01); *A61B 5/0816* (2013.01); *A61B 5/4809* (2013.01);
(Continued)

(58) Field of Classification Search
CPC ... A61B 5/4812; A61B 5/0816; A61B 5/4809; A61B 5/4818; A61B 5/6803; A61B 5/7264; A61B 7/003
(Continued)

(56) References Cited

U.S. PATENT DOCUMENTS 6,168,568 B1 * 1/2001 Gavriely ............... A61B 5/087
600/529
6,261,238 B1 * 7/2001 Gavriely ............... A61B 5/087
600/532
(Continued)

FOREIGN PATENT DOCUMENTS

WO    WO 2010054481 A1 *  5/2010    .......... A61B 5/0803
WO        2013179254        12/2013

OTHER PUBLICATIONS

Popovic, D., et al. "Sleep/Wake Classification Using Head Actigraphy, Snoring and Airflow Signals"; Conference: Sleep 2009, vol. 32, Abstract Supplement, 2009; 1 page.
(Continued)

*Primary Examiner* — Navin Natnithithadha
(74) *Attorney, Agent, or Firm* — Middleton Reutlinger

(57) ABSTRACT

Described herein are various embodiments of a method and system for sleep detection. For example, in one embodiment, a method is described for automatically characterizing digitized breath sounds recorded from a subject over time as indicative of the subject being one of asleep and awake. This method comprises identify individual breathing cycles in a given segment of the recorded breath sounds; calculating one or more preset breathing cycle characteristics from the identified breathing cycles; evaluating a relative regularity of the calculated characteristics for the given segment; and upon the relative regularity satisfying a preset high regularity condition, outputting a sleep status indicator that the subject was likely asleep during the segment, otherwise outputting a wake indicator that the subject was likely awake during the segment.

13 Claims, 17 Drawing Sheets

(52) U.S. Cl.
CPC .......... *A61B 5/4818* (2013.01); *A61B 5/6803* (2013.01); *A61B 5/7264* (2013.01); *A61B 7/003* (2013.01)

(58) Field of Classification Search
USPC .................................................. 600/529–543
See application file for complete search history.

(56) References Cited

U.S. PATENT DOCUMENTS

| | | | | |
|---|---|---|---|---|
| 6,773,404 | B2* | 8/2004 | Poezevera | A61N 1/3601 600/301 |
| 6,890,306 | B2* | 5/2005 | Poezevera | A61B 5/0809 600/529 |
| 7,395,115 | B2* | 7/2008 | Poezevera | A61N 1/3601 607/20 |
| 9,232,910 | B2* | 1/2016 | Alshaer | A61B 5/0803 |
| 2003/0130589 | A1* | 7/2003 | Poezevera | A61B 5/0809 600/533 |
| 2003/0163059 | A1* | 8/2003 | Poezevera | A61N 1/3601 600/534 |
| 2004/0006375 | A1* | 1/2004 | Poezevera | A61N 1/3601 607/17 |
| 2006/0212273 | A1* | 9/2006 | Krausman | A61B 5/087 702/189 |
| 2011/0288431 | A1* | 11/2011 | Alshaer | A61B 5/0803 600/534 |
| 2012/0125337 | A1* | 5/2012 | Asanoi | A61B 5/0816 128/204.23 |

OTHER PUBLICATIONS

Popovic D., et al. "Sleep/Wake Classification with Head Actigraphy"; Conference: Sleep 2011, vol. 34, Abstract Supplement and Poster; 2 pages.

Engoren, M. "Approximate Entropy of Respiratory Rate and Tidal Volume During Weaning From Mechanical Ventilation" Crit Care Med, vol. 26, pp. 1817-1823, Nov. 1998.

* cited by examiner

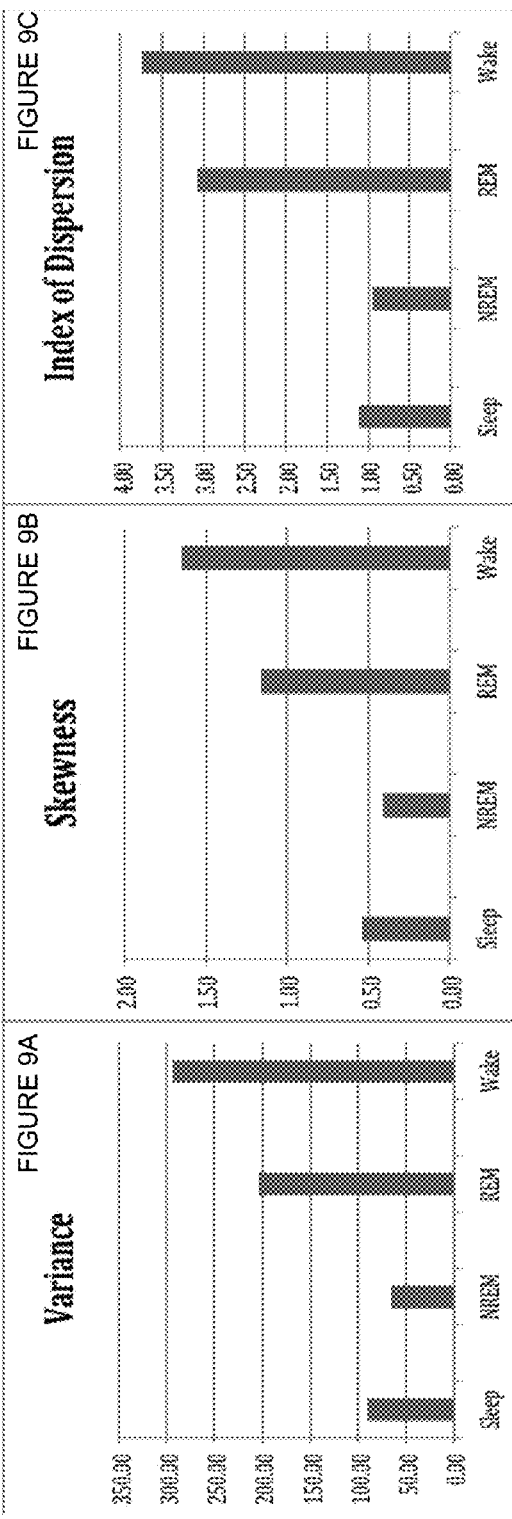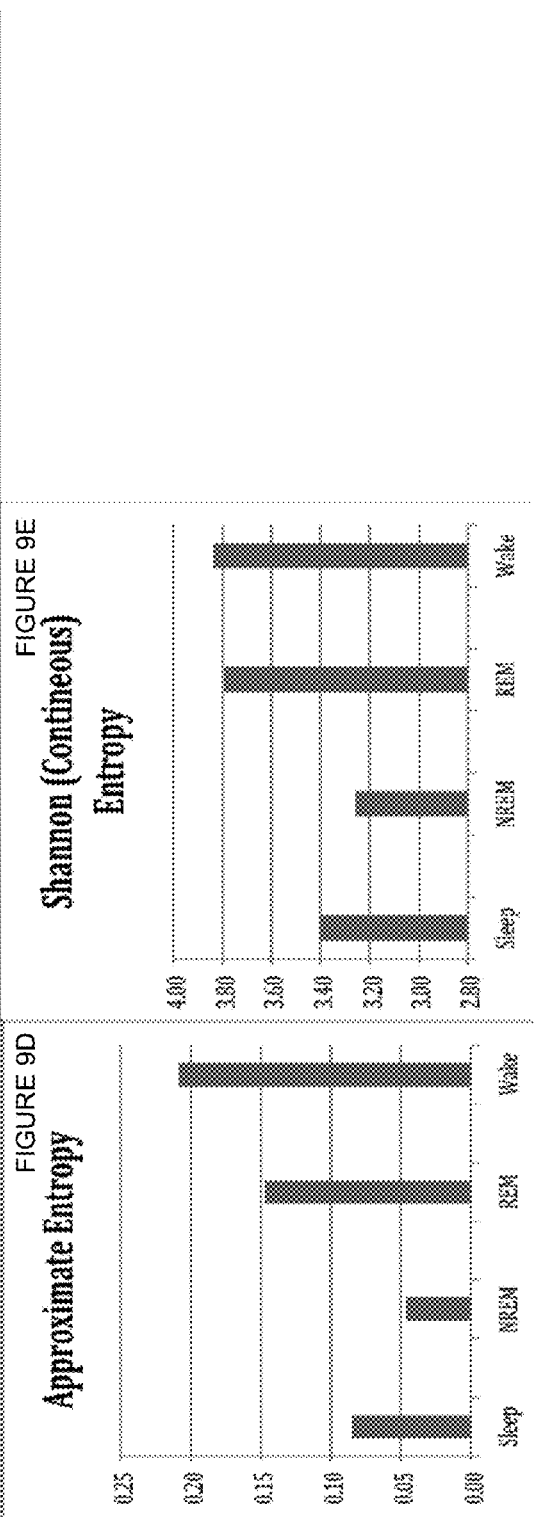
FIGURES 9A - 9E

METHOD AND SYSTEM FOR SLEEP DETECTION

FIELD OF THE DISCLOSURE

The present disclosure relates to sleep and breathing studies and, in particular, to a method and system for sleep detection.

BACKGROUND

Sleep apnea severity is quantified by the apnea hypopnea index (AHI), which is the frequency of apnea and hypopneas per hour. In a sleep laboratory, the AHI is expressed as the frequency of apnea and hypopneas per hour of sleep. Thus, knowledge of sleep time as opposed to overall recording time is important for accurate estimation of the sleep apnea severity. Other applications to the determination of sleep time may also be relevant in conducting accurate sleep studies, as can such indication provide useful information in respect of other breathing or physiological studies that may be more or less related to sleep apnea.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

A need exists for a method and system for sleep detection that overcome some of the drawbacks of known techniques, or at least, provide a useful alternative thereto. Some aspects of this disclosure provide examples of such systems and methods.

In accordance with one aspect, there is provided a method for automatically characterizing digitized breath sounds recorded from a subject over time as indicative of the subject being one of asleep and awake, the method comprising: identify individual breathing cycles in a given segment of said recorded breath sounds; calculating one or more preset breathing cycle characteristics from said identified breathing cycles; evaluating a relative regularity of said calculated characteristics for said given segment; and upon said relative regularity satisfying a preset high regularity condition, outputting a sleep status indicator that the subject was likely asleep during said segment; otherwise or upon said relative regularity satisfying a preset low regularity condition, outputting a wake indicator that the subject was likely awake during said segment.

In one embodiment, said sleep status indicator comprises either of a NREM sleep indicator and a REM sleep indicator, wherein said preset high regularity condition encompasses two distinct high regularity conditions, and wherein satisfying a higher one of said high regularity conditions triggers said NREM sleep indicator whereas satisfying a lower one of said low regularity conditions triggers said REM sleep indicator.

In one embodiment, said one or more preset breathing cycle characteristics comprise at least one of an inter-breath interval and an inter-breath cycle energy.

In one embodiment, the method further comprises extracting one or more designated features from said one or more preset characteristics, and wherein said evaluating step comprises evaluating said regularity as a function of said extracted features.

In one embodiment, said one or more features comprise at least one of entropy, dispersion and variance.

In one embodiment, the method further comprises compiling each said wake or sleep indicator for each said segment to compute an actual sleep time to be associated with said breath sound recording during which the subject is asleep.

In accordance with another aspect, there is provided a method for automatically characterizing digitized breath sounds recorded from a subject over time as indicative of one of a sleep status and a wake status, the method comprising: identify individual breathing cycles in a given segment of said recorded breath sounds; calculating a relative regularity of said identified breathing cycles; comparing said relative regularity with one or more preset regularity conditions to output at least one of a high regularity and a low regularity indicator indicative of the sleep status and the wake status, respectively; and at least one of: extracting one or more designated snore-related features from said recorded breath sounds in said given segment previously determined to distinguish snoring sounds from non-snoring sounds to identify instances of snoring during said segment; and extracting one or more designated upper airway relaxation-related features from said recorded breath sounds in said given segment previously determined to distinguish relatively high upper airway narrowing instances from relatively low upper airway narrowing instances, to identify instances of relatively high upper airway relaxation; and confirming the sleep status indicated by said low regularity indicator upon said evaluating said extracted snore-related features identifying one or more said instances of snoring during said segment and/or upon said evaluating said extracted upper airway relaxation features identifying a relatively high upper airway relaxation during said segment.

In one embodiment, said sleep status comprises either of a NREM sleep status and a REM sleep status, wherein said preset high regularity condition encompasses two distinct high regularity conditions, and wherein satisfying a higher one of said high regularity conditions triggers said NREM sleep status whereas satisfying a lower one of said high regularity conditions triggers said REM sleep status.

In one embodiment, said NREM sleep status is output irrespective of whether either of said instances of relatively high upper airway narrowing and said instances of snoring are identified.

In one embodiment, said REM sleep status is output only upon the sleep status being confirmed by said instances of relatively high upper airway narrowing and/or said instances of snoring being identified.

In accordance with another aspect, there is provided a device for automatically characterizing digitized breath sounds recorded from a subject over time as indicative of one of a sleep status and a wake status, the device comprising: a recording device responsive to breath sounds; one or more processors; and one or more data storage devices having stored thereon statements and instructions for implementation by said processor in performing the above methods.

In one embodiment, said recording device comprises a microphone embedded within a face mask to be worn on the subject's face while sleeping such that said microphone is disposed above a nose and mouth area of the subject's face and receptive of breath sounds and airflow.

Other aspects, features and/or advantages will become more apparent upon reading of the following non-restrictive description of specific embodiments, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 8A is an illustrative waveform plot of breathing sounds acquired from a single breath showing both an inspiration phase and an expiration phase, whereas

FIGS. 9A to 9E are bar charts of selected features extracted from recorded breath sounds to automatically distinguish between sleep statuses based on inter-breath interval (IBI) regularity, in accordance with one embodiment of the invention;

DETAILED DESCRIPTION

Figure 1:
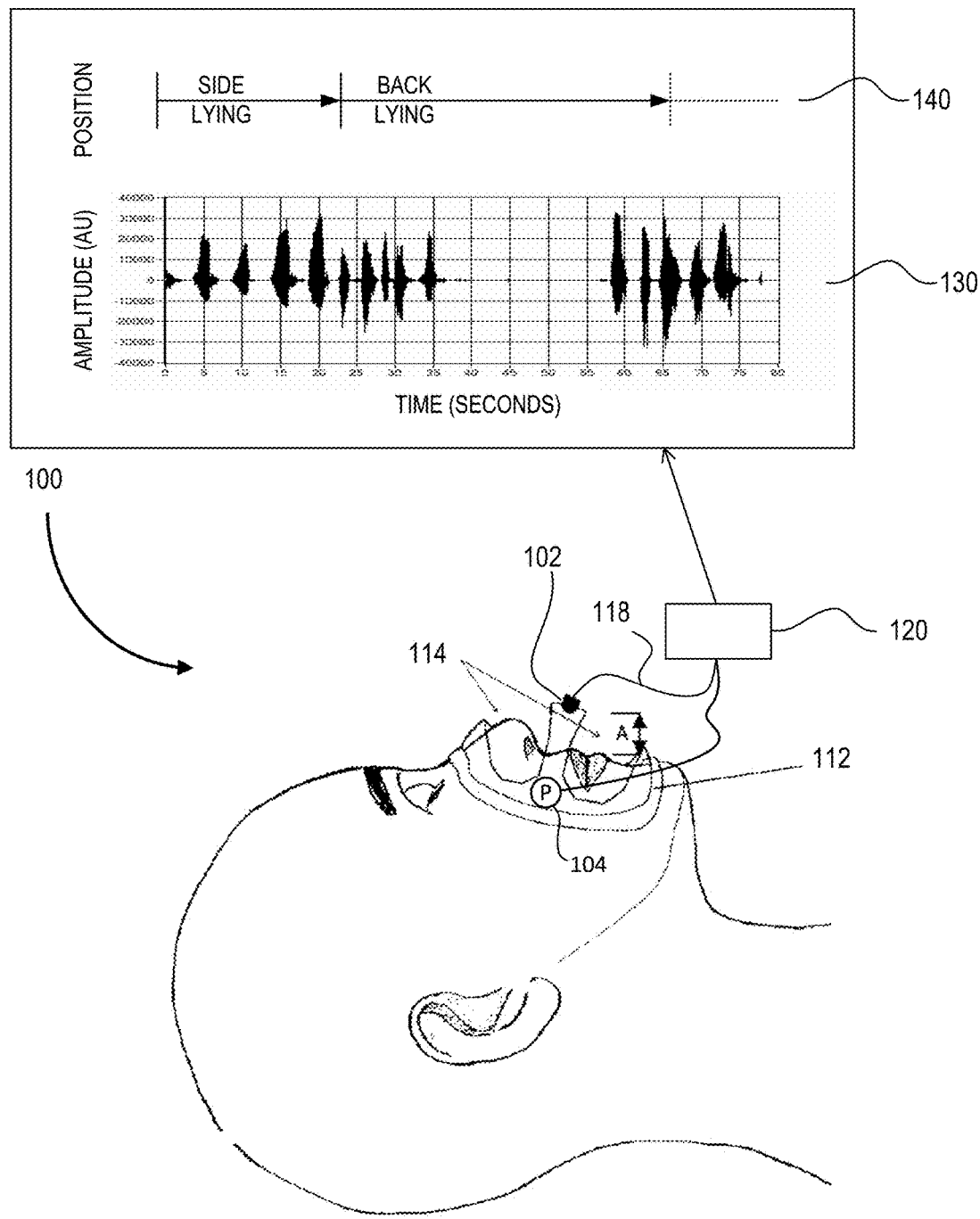
FIG. 1 is a diagram of a system comprising a mask to be positioned on a subject's face to record a breathing signal and a head position signal for use in breathing and/or sleep studies, in accordance with an exemplary embodiment of the invention.

With reference to the disclosure herein and the appended figures, various methods and systems for sleep detection, for example within the context of a breathing and/or sleeping condition identification, characterization and/or diagnosis methods and devices, will now be described. Namely, the following describes various methods and devices that can be used, in combination or alone, to achieve various levels of breathing and/or sleeping condition identification, characterization and/or diagnosis. In some embodiments, such methods and devices rely, at least in part, on the analysis of breath-related sounds. For example, in some embodiments, the methods and devices described herein can be used to detect sleep apnea via acoustic breath sound analysis, such as from overnight breath sound recordings and the like, and in some embodiments, to further quantify a severity of this disorder in a given subject, to distinguish between OSA and CSA, and/or achieve other related characterizations of the subject's condition. Such results present significant improvements in the provision of a less invasive approach to sleep apnea identification, characterization and/or diagnosis, particularly as compared to PSG and other such techniques. Namely, and in accordance with some embodiments, useable results can be achieved using as few as a single non-invasive acoustic breathing sound channel to achieve sleep apnea identification, characterization and/or diagnosis, which may further include characterization of a severity of the identified apnea and/or differentiation between OSA and CSA, the accuracy of which may be significantly improved by the provision of accurate sleep detection, as contemplated by the embodiments disclosed herein.

For instance, a typical person will take 10 to 15 minutes to fall asleep, and, when suffering from some form of sleep apnea, will wake up several times during the night. Having a relatively accurate measure of this person's actual sleep onset, awakenings and overall sleep time, for example, may thus provide useful information in the assessment of this person's sleeping and/or breathing condition. Further information, such as a determination of this person's passage through the various sleep stages, namely stages 1 to 4 of non-rapid-eye movement (NREM) sleep, and rapid eye movement (REM) sleep, as well as potential arousals during the overall sleep period, may provide further insight as to a patient's condition. For the sake of clarity, wakefulness will be distinguished herein from arousals, in that wakefulness relates to full awakenings where a subject wakes up from sleep but does not fall back asleep quickly, as compared to arousals defined as brief awakenings from sleep followed a relatively quick return to sleep.

In accordance with some embodiments, a system and method are provided in which sleep may be accurately distinguished from wakefulness, sleep onset may be accurately identified, and/or sleep time may be accurately quantified based, at least in part, on the analysis of recorded breath sounds. For instance, the methods and systems described herein are configured to extract various features from recorded breath sounds that, as demonstrated herein, can lead to an accurate determination of at least some of these sleep characteristics. This approach, optionally in combination with other techniques considered herein for sleeping and breathing condition identification, characterization and/or diagnosis, can thus provide a more complete patient assessment.

With reference now to FIG. 1, and in accordance with one embodiment, a system 100 for use in breathing and/or sleep studies will now be described. In this embodiment, the system 100 generally provides for the recordal of breath sound data, in this example, via one or more transducers, such as microphone 102, disposed at a distance A from a nose and mouth area of a candidate's face in a face mask 112 to be worn by the candidate during testing. For example, the mask may be worn overnight to ultimately detect various sleep cycles/phases and, in some embodiments, provide insight in the study of various sleep-related disorders such as sleep apnea. As schematically depicted, the one or more transducers 102 are operatively coupled to a data recording/processing device 120 for recording breath sound data, illustratively depicted by raw signal plot 130, for processing.

In this example, the microphone 102 is coupled in or to a loose fitting full face mask 112 which includes at least one opening 114 to allow for ease of breathing, and provides for a communication path 118, be it wired and/or wireless, from the microphone 102 to the recording/processing device 120.

The system 100 further comprises an optional positional sensor 104 to be worn by the candidate to monitor a position (e.g. head position) thereof during sleep, for example. The positional sensor 104, for example a three-axis (3D) accelerometer such as a micro-electro-mechanical systems (MEMS) accelerometer, is operatively coupled to the recording/processing device 120 in this example to record a 3D sensor orientation and ultimately extrapolate a sleeping position (orientation) 140 of the candidate, which sleeping position may be correlated with breath-sound analyses to further characterize the candidate's condition. For example, different sleeping positions may be extrapolated from 1D, 2D and particularly 3D positional data, which positions may include but are not limited to, side-lying, back-lying, front-lying, level of incline (e.g. pillow use), etc. In some embodiments, identification of a positional correlation with an observed breathing disorder may be used to prescribe or recommend appropriate treatment of the candidate's condition, for instance in recommending sleeping arrangements that may encourage the avoidance of problematic positioning and thus reduce the occurrence of breathing disturbances. Furthermore, positional data may be used to identify subject movements, which may be indicative of the subject waking-up, for example, in response to an apneic/hypopneic event. As will be discussed in greater detail below, monitoring patient movement via positional data may also or alternatively provide some indication as to sleep onset, arousals and awakenings, for instance by observing changes in the patient's movement frequency, amplitude, and the like.

In some embodiments, the positional sensor 104 may be mounted or otherwise coupled to the mask 112 thereby allowing for extrapolation of the orientation of the candidate's head during sleep, which, unless the mask 112 has been dislodged from its original position, should be consistent with a monitored orientation of the mask. Similarly, a general sleeping position of the candidate may be extrapolated from the positional data so to identify and track, and ultimately correlate a position of the candidate while sleeping with detected disturbances in the candidate's breathing, as characterized for instance via parallel breath sound analysis. Alternatively, or in addition thereto, a positional sensor may be worn by the candidate via other means distinct from the mask 112, but again for the purpose of tracking and correlating a position of the subject while sleeping with identified breathing disturbances, and/or for tracking variations in movement frequency, etc., for the purpose of tracking sleep cycles, arousals, wakefulness and/or awakenings, for example.

Figure 2:
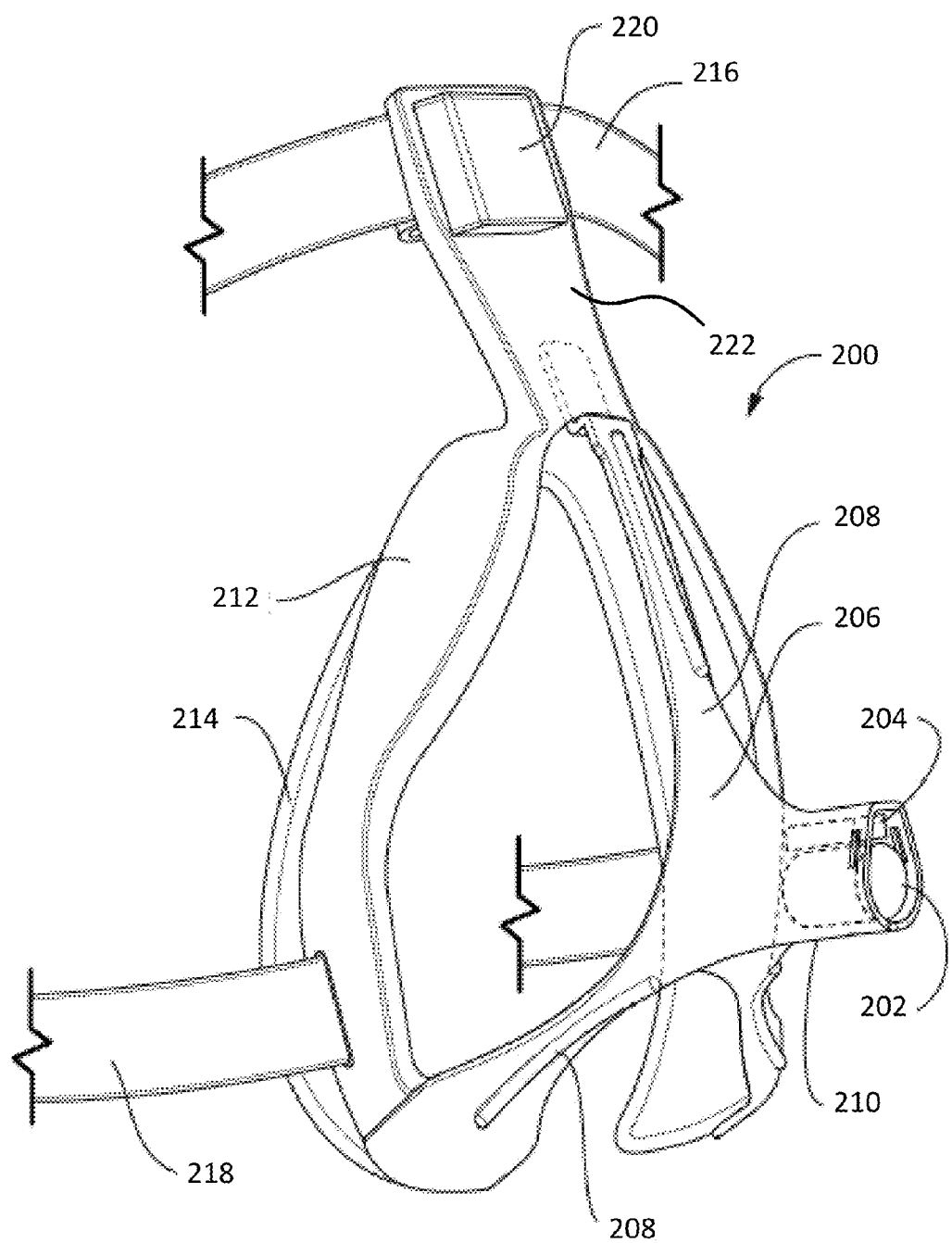
FIG. 2 is a perspective view of another mask for use, for example, in the system of FIG. 1, in accordance with another exemplary embodiment of the invention.

FIG. 2 provides another example of a mask 200 usable in acquiring breathing sounds and positional data suitable in the present context. In this example, the mask 200 generally comprises at least one transducer, such as microphone 202, a positional sensor, such as MEMS accelerometer 204, and a support structure 206 for supporting same above a nose and mouth area of the subject's face. The support structure 206 is generally shaped and configured to rest on the subject's face and thereby delineate the nose and mouth area thereof, and comprises two or more outwardly projecting limbs 208 (e.g. three limbs in this example) that, upon positioning the mask 200, converge into a transducer supporting portion 210 for supporting microphone 202 and sensor 204 at a distance from this area.

The support structure further comprises an optional frame 212 and face resting portion 214 shaped and configured to contour the face of the subject and at least partially circumscribe the nose and mouth area of the subject's face, thereby facilitating proper positioning of the mask on the subject's face and providing for greater comfort. A restraining mechanism, such as head straps 216 and 218, can be used to secure the mask to the subject's face and thereby increase the likelihood that the mask will remain in the proper position and alignment during use, e.g. even when the subject is sleeping in monitoring certain breathing disorders such as sleep apnea. Proper positioning and alignment may further increase accuracy and reliability of positional data acquired via sensor 204 in extrapolating a more accurate representation of the candidate's position/movement during sleep, arousals and/or wakefulness.

In this embodiment, the mask 200 further comprises an integrated recording device 220, such as a digital recording device or the like, configured for operative coupling to the at least one transducer 202 and sensor 204, such that sound and/or airflow signals generated by the at least one transducer can be captured and stored for further processing along with positional data representative of the candidate's sleeping position, for example via one or more data processing modules (not shown). In this particular embodiment, the recording device 220 is disposed on a frontal member 222 of the support structure 206, thereby reducing an obtrusiveness thereof while remaining in close proximity to the at least one transducer 202 and sensor 204 so to facilitate signal transfer therefrom for recordal. In providing an integrated recording device, the mask 200 can effectively be used as a self-contained respiratory monitoring device, wherein data representative of the subject's breathing and position can be stored locally on the mask and transferred, when convenient, to a remotely located respiratory diagnostic center, for example. Further details as to the design, features and use of mask 200 are provided in U.S. Patent Application Publication No. 2011/0092839 and International Application Publication No. WO 2012/037641, the entire contents of each one of which is hereby incorporated herein by reference.

Figure 3:
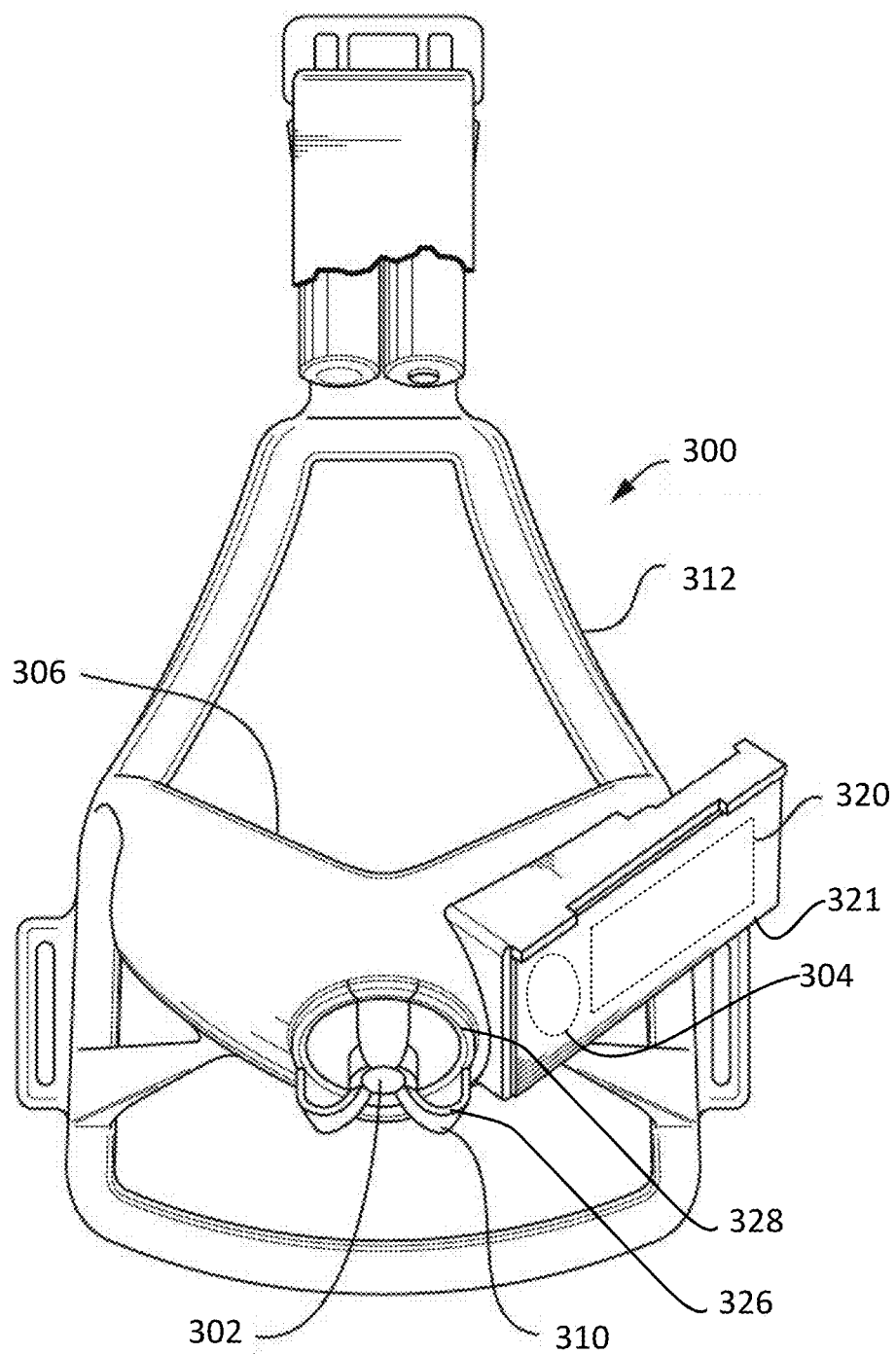
FIGS. 3 and 4 are front and side views, respectively, of another mask for use, for example, in the system of FIG. 1, in accordance with another exemplary embodiment of the invention.
Figure 4:
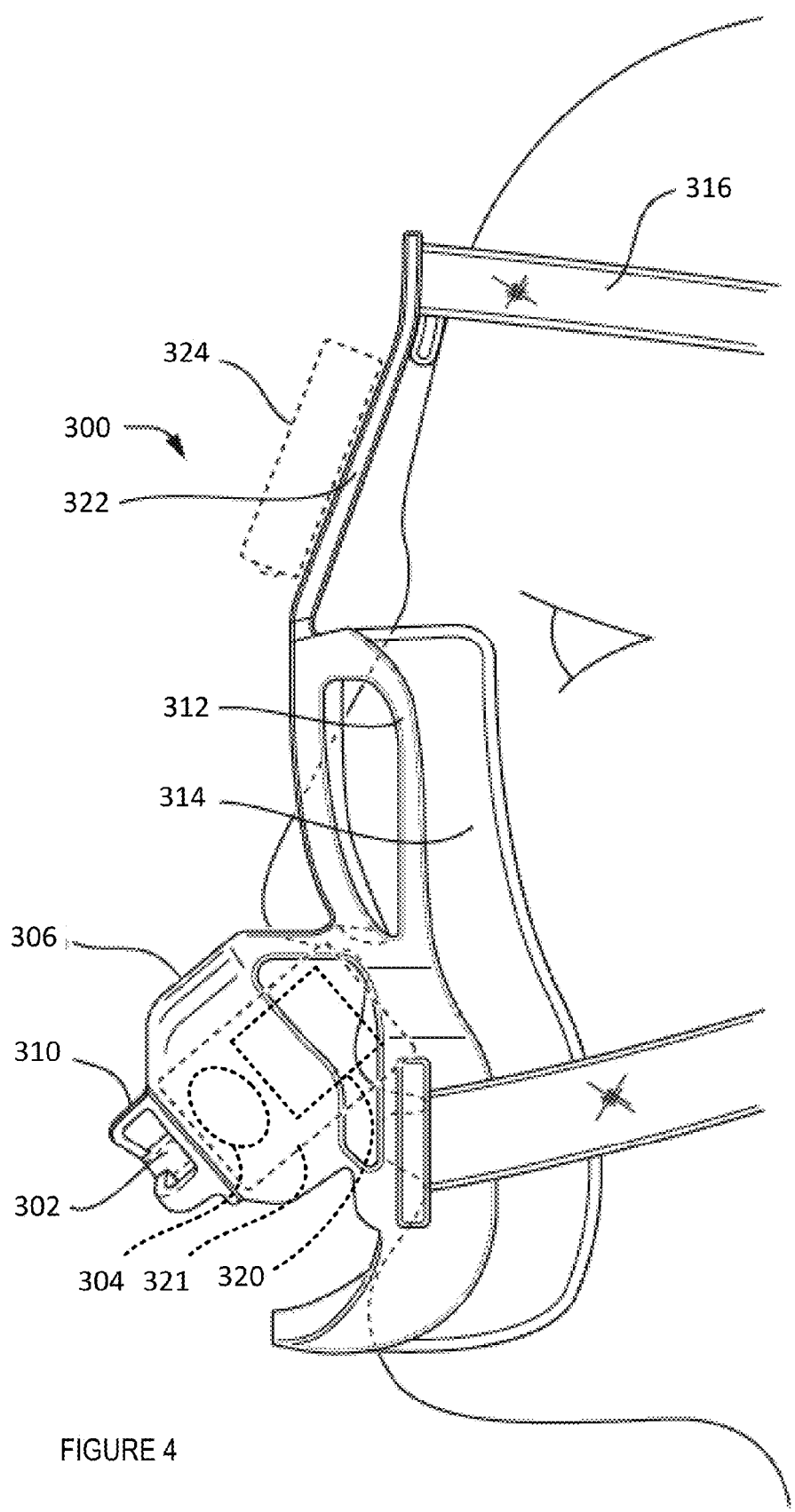

FIGS. 3 and 4 provide yet another example of a mask 300 usable in acquiring breathing sounds and positional data suitable in the present context. In this example, the mask 300 comprises at least one transducer, such as microphone 302, and a support structure 306 for supporting same above a nose and mouth area of the subject's face. A positional sensor, such as MEMS accelerometer 304, is schematically integrated within the casing 321 of recording device 320 (discussed below). The support structure 306 is generally shaped and configured to rest on the subject's face and extend outwardly therefrom over a nose and mouth area thereof to provide a transducer supporting portion 310 for supporting the microphone 302, upon positioning the mask, at a distance from this area.

In this example, the support structure 306 is shaped and configured to support the transducer 302 above the nose and mouth area at a preset orientation in relation thereto, wherein the preset orientation may comprise one or more of a preset position and a preset angle to intercept airflow produced by both the subject's nose and mouth. For example, in one embodiment, the preset orientation may be preset as a function of an estimated intersection between nasal and oral airflow, for example based on an observed or calculated average intersection between such airflows. For instance, in one embodiment, the preset orientation may comprise a preset position that, upon positioning the mask on the subject's face, is substantially laterally centered relative to the subject's face and longitudinally substantially in line with or below the subject's mouth, thus generally intercepting oral and nasal airflow.

In a same or alternative embodiment, the preset orientation may comprise a preset angle that aligns the microphone, or a principle responsiveness axis thereof, along a line more or less representative of an averaging between general oral and nasal airflows. For instance, in one embodiment, the orientation angle is preset to more or less bisect an angle formed by the transducer's preset position relative to the subject's nose (i.e. nostrils) and mouth. This bisecting angle, which should be construed within the present context to represent an angle more or less directing the transducer's principal responsiveness axis toward a point somewhere between the wearer's nose and mouth, may be determined as a function of measured, observed and/or otherwise estimated nasal and oral breathing patterns, so to improve or enhance the transducer's general responsiveness to airflow originating from the nose and/or mouth of the candidate. Generally, the preset orientation may thus, in accordance with one embodiment of the invention, comprise a preset angle that, upon positioning the mask on the subject's face, substantially aligns the transducer with a point between the subject's nose and mouth.

In this embodiment, the support structure 306 generally comprises two outwardly projecting limbs that flow continuously one within the other toward the transducer supporting portion 310 in defining a funneling shape that substantially converges toward this transducer supporting portion, thus effectively redirecting nasal and/or oral airflow toward the transducer 302 and allowing for effective monitoring of airflow produced by both the subject's nose and mouth while breathing. Accordingly, breathing airflow, which will generally more or less diverge laterally from the candidate's nostrils as it is projected more or less obliquely downward therefrom can be effectively collected, at least partially, by the generally concave support structure 306 to be substantially funneled thereby toward the transducer 302. Accordingly, in this embodiment, not only is the transducer's preset orientation generally selected as a function of an estimated nasal and oral airflow intersection, the general funneling shape of the support structure 306 will further redirect at least a portion of laterally diverging nasal (and oral) airflow toward the transducer 302. Similarly, though not explicitly depicted herein, the same generally concave shape of the funneling support structure 306 will, partly due to its upwardly tilted orientation in this embodiment, also at least partially redirect longitudinally divergent airflow toward the transducer 302.

The transducer-supporting portion 310 of the support structure 306 further comprises one or more (three in this embodiment) transducer supporting bridges or limbs 326 extending from a transducer-surrounding aperture 328 defined within the support structure 306. In this embodiment, the provision of bridging limbs 326 may allow for a general reduction in airflow resistance, which may result in substantially reduced dead space. For example, while the general funneling shape of the support structure 306 allows for a redirection of airflow toward the transducer 302, the bridged aperture 328 allows for this flow of air to continue beyond the transducer 302, and thereby reduce the likelihood of this flowing air pooling within the mask and/or flowing back onto itself, which could otherwise lead to a generally uncomfortable warm/humid flow of breath back in the candidate's face (and which could thus be breathed in again), and/or lead to unusual flow patterns and/or sounds that could further complicate data processing techniques in accounting for these patterns.

The support structure 306 further comprises an optional frame 312 and face resting portion 314 shaped and configured to contour the face of the subject and at least partially circumscribe the nose and mouth area of the subject's face, thereby facilitating proper positioning of the mask on the subject's face and providing for greater comfort. A restraining mechanism, such as head straps 316, can be used to secure the mask to the subject's face and thereby increase the likelihood that the mask will remain in the proper position and alignment during use, even when the subject is sleeping, for example, in monitoring and diagnosing certain common breathing disorders. It will be appreciated that the data analysis techniques described below may also be applicable, in some conditions, in monitoring and diagnosing a subject's breathing when awake.

In this embodiment, the mask 300 further comprises a recording device 320, such as a digital recording device or the like, configured for operative coupling to the at least one transducer 302 and sensor 304, such that breath sound signals generated by the at least one transducer 304, and positional data generated by the sensor 304, can be captured and stored for further processing. In this particular embodiment, the recording device 320 is encased within casing 321 integrally coupled to one of the limbs of the support structure 306, thereby reducing an obtrusiveness thereof while remaining in close proximity to the at least one transducer 302 and sensor 304 so to facilitate signal transfer therefrom for recordal. A battery pack 324, operatively coupled to the recording device 320, is provided on a frontal member 322 of the mask 300 to power the recording device and transducer in acquiring data free of any external wiring or the like. In providing an integrated and self-supported recording device, the mask 300 can effectively be used as a self-contained respiratory monitoring device, wherein data representative of the subject's breathing and position can be stored locally on the mask and transferred, when convenient, to a remotely located respiratory diagnostic center, for example.

Further details as to the design, features and use of mask 300 are provided in International Application Publication No. WO 2012/037641, the entire content of which is incorporated herein by reference.

As will be appreciated by the person of ordinary skill in the art, the general shape and design of the above-described masks (200, 300) can provide, in different embodiments, for an improved responsiveness to airflow produced by the subject while breathing, and that irrespective of whether the subject is breathing through the nose or mouth, predominantly through one or the other, or through both substantially equally. Namely, the ready positioning of an appropriate transducer responsive to airflow relative to the nose and mouth area of the subject's face is provided for by the general spatial configuration of these masks. Accordingly, great improvements in data quality, reliability and reproducibility can be achieved, and that, generally without the assistance or presence of a health care provider, which is generally required with previously known systems.

Furthermore, it will be appreciated that different manufacturing techniques and materials may be considered in manufacturing the above and similar masks, for example as described below, without departing from the general scope and nature of the present disclosure. For example, the entire mask may be molded in a single material, or fashioned together from differently molded or otherwise fabricated parts. For example, the outwardly projecting nosepiece of the mask may comprise one part, to be assembled with the frame and face-resting portion of the mask. Alternatively, the frame and nosepiece may be manufactured of a single part, and fitted to the face-resting portion thereafter. As will be further appreciated, more or less parts may be included in different embodiments of these masks, while still providing similar results. For example, the nose piece, or an equivalent variant thereto, could be manufactured to rest directly on the subject's face, without the need for a substantial frame or face resting portions. Alternatively or in addition, different numbers of outwardly projecting limbs (e.g. two, three, four, etc.) or structures may be considered to provide similar results.

In general, the at least one transducer in the above examples, and their equivalents, is responsive to sound and/or airflow for generating a data signal representative of breathing sounds to be used in implementing different embodiments of the below-described methods. For example, in one embodiment, two microphones may be provided in the transducer support portion, wherein one of these microphones may be predominantly responsive to sound, whereas the other may be predominantly responsive to airflow. For example, the microphone configured to be predominantly responsive to airflow may be more sensitive to air pressure variations than the other. In addition or alternatively, the microphone configured to be predominantly responsive to sound may be covered with a material that is not porous to air. In addition or alternatively, the microphone configured to be predominantly responsive to sound may be oriented away from the subject's nose and mouth so to reduce an air impact on the diaphragm of this microphone produced by the subject's breathing airflow. In other embodiments, a microphone predominantly responsive to airflow may be positioned in the transducer support portion in line with the subject's nose and mouth, while another microphone may be positioned to the side or on the periphery of the mask to thereby reduce an influence of airflow thereon. In some of these embodiments, the recorded sound from the peripheral microphone, or again from the microphone predominantly responsive to sound, may in fact be used to isolate the airflow signal recorded in the nosepiece, by filtering out the sound signal recorded thereby, for example.

In the embodiments of FIGS. 1 to 4, however, a single microphone may alternatively be used to capture both sound and airflow, wherein each signal may be optionally distinguished and at least partially isolated via one or more signal processing techniques, for example, wherein a turbulent signal component (e.g. airflow on microphone diaphragm) could be removed from other acoustic signal components (e.g. snoring). Such techniques could include, but are not limited to adaptive filtering, harmonics to noise ratio, removing harmonics from a sound recording, wavelet filtering, etc.

In each of the above examples, the device may be implemented using a single type of transducer, for example one or more microphones which may in fact be identical. It will be appreciated however that other types of transducers, particularly responsive to airflow, may be considered herein without departing from the general scope and nature of the present disclosure. For example, a pressure sensor or airflow monitor may be used instead of a microphone to yield similar results in capturing an airflow produced by the subject while breathing.

It will be appreciated by the skilled artisan that different types of masks, or other means for recording breath sounds, may be considered herein without departing from the general scope and nature of the present disclosure. Namely, while the above examples provide for one means for acquiring breath sound data in implementing the below-described analysis methods, other means will be readily apparent to the person of ordinary skill in the art and should thus be considered to fall within the context of the present disclosure. For example, different microphone setups may be considered to provide similar effects, such as, but not limited to, positioning a microphone on the lip, the trachea, or on the forehead of the candidate, or again by providing a floating microphone disposed above the candidate's face or head during sleep. These and other variations will be readily apparent to the skilled artisan and therefore intended to fall within the general scope and nature of the present disclosure.

In the above examples, acquired breath sound and positional data is generally communicated to data recording/processing device 120, 220, 320, which may comprise a single self-contained device, or a number of distinct and communicatively coupled or coupleable devices configured to provide complementary resources in implementing the below-described methods. Namely, the recording/processing device may comprise a distinctly implemented device operatively coupled to one or more breath sound transducers and positional sensor for communication of data acquired thereby via, for example, one or more data communication media such as wires, cables, optical fibres, and the like, and/or one or more wireless data transfer protocols, as would be readily appreciated by one of ordinary skill in the art. A distinct recording device may, however, in accordance with another embodiment, be implemented integrally with the mask, and used to later communicate recorded data, be it raw and/or preprocessed data, to a remote or distinct processing device. Similarly, common or distinct recording devices may be used at the forefront to acquire and record breath sound and positional data, respectively, for downstream processing and correlation in accordance with different embodiments of the invention. As will be appreciated by the skilled artisan, the processing module(s) may further be coupled to, or operated in conjunction with, an external processing and/or interfacing device, such as a local or remote computing device or platform provided for the further processing and/or display of raw and/or processed data, or again for the interactive display of system implementation data, protocols and/or diagnostics tools.

Figure 15:
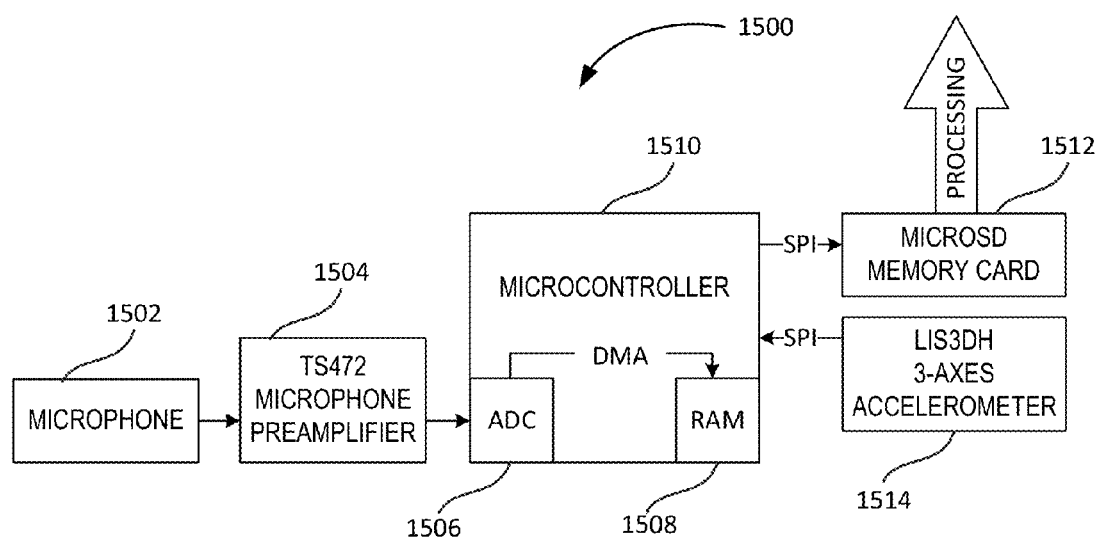
FIG. 15 is a schematic diagram of hardware integrated within a self-contained mask for use in breathing and/or sleeping studies, in accordance with one embodiment of the invention.

With reference to FIG. 15, a schematic diagram of an integrated hardware architecture 1500 of a mask, such as shown in FIGS. 1 to 4, encompassing self-contained recording capabilities, will now be described, in accordance with one embodiment of the invention. In this embodiment, a microphone 1502 responds to sound and/or airflow generated by a subject while breathing, and communicates a breath-related signal to a microphone preamplifier 1504 (e.g. Model TS472 by STMicroelectronics), which is then processed through analog to digital converter 1506 and random access memory (RAM) 1508 via a direct memory access controller (DMA) of microcontroller 1510, for ultimate storage on microSD card 1512 (e.g. via a serial peripheral interface (SPI), or the like). It will be appreciated that RAM 1508 may consist of internal or external microcontroller memory. Concurrently, positional data is acquired via a 3-axes accelerometer 1514 (e.g. Model LIS3DH by STMicroelectronics) and transferred via SPI by microcontroller 1510 to the microSD card 1512. The microSD card 1512 may then be transferred to an appropriate processing device where data stored thereon may be uploaded and processed, as discussed in greater detail below.

Figure 16:
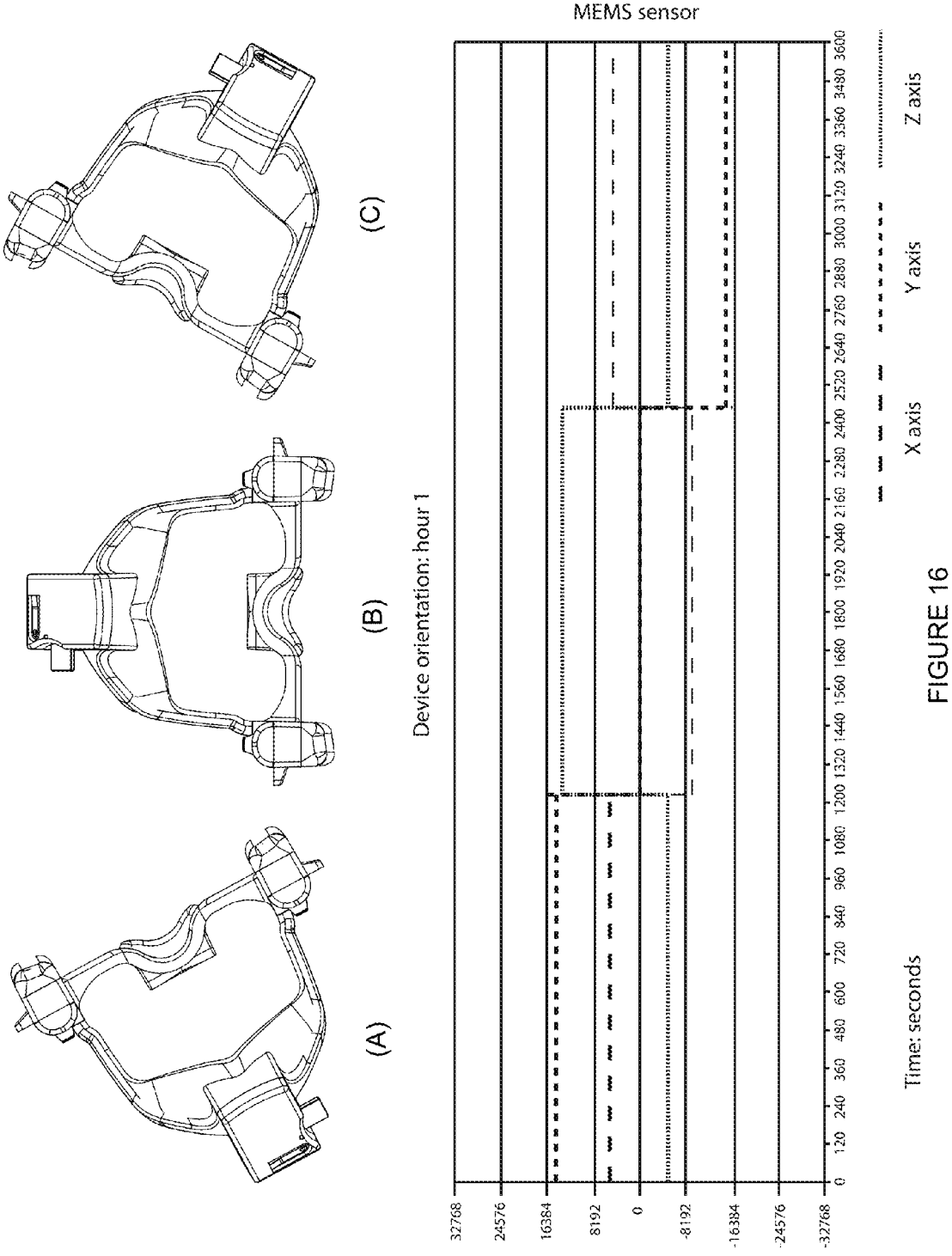
FIG. 16 is a plot of accelerometric data recorded over a simulated one-hour sleep monitoring event via an accelerometer embedded within a mask, such as shown in FIGS. 1 to 4, and correlated with an orientation of the recording mask, in accordance with one embodiment of the invention.

In one embodiment, acceleration data for all three axes is sampled simultaneously with sound and/or airflow data from the microphone 1502, and stored in separate files over the entire recording session. Both breath and position data is later uploaded from the memory card 1512 for processing. Accordingly, accelerometric data, for example from data collected at sampling rates of 5.43 Hz, or as otherwise required, may be processed to identify an orientation of the mask and thus allow correlation with an identified sleep apnea condition. This data may further allow for the detection of subject movements that may be indicative of subject awakenings and/or arousals, for example in response to an apneic event, and reductions and/or changes in movement frequency/amplitude that may be indicative of sleep onset, for example. Alternatively, or in addition, the accelerometric data may be correlated to interrupts received from the accelerometer which, when equipped with configurable thresholds, can be adjusted to provide appropriate resolution, as will be appreciated by the skilled artisan. An example one hour plot is illustrated in FIG. 16, with the vertical units corresponding to 16 bit raw accelerometric data, showing each of the three axes of the accelerometer concurrently, configured to 2 g full scale. FIG. 16 is intended to show a simulated one hour sleep monitoring event, in which the position of the subject is extrapolated from the orientation of the mask frame. In this case, the subject can be seen to migrate from an initial right side-lying position, as shown in orientation (A), then to a flat back-lying head position as shown in orientation (B), and finally to a left side-lying position as shown in orientation (C).

As will be appreciated by the skilled artisan, different components and/or component configurations may be implemented to provide similar results. For example, in one embodiment, a microcontroller selected from the ARM Cortex-M MCU family may be selected, which offers an improved functional and cost effective platform for embedded applications with 16 bit onboard ADC, SD host controller and high RAM-to-flash ratio. Another example may include a digital MEMS microphone or the like in leveraging their small form factor, high noise immunity, and low power consumption, for example.

Figure 5A:
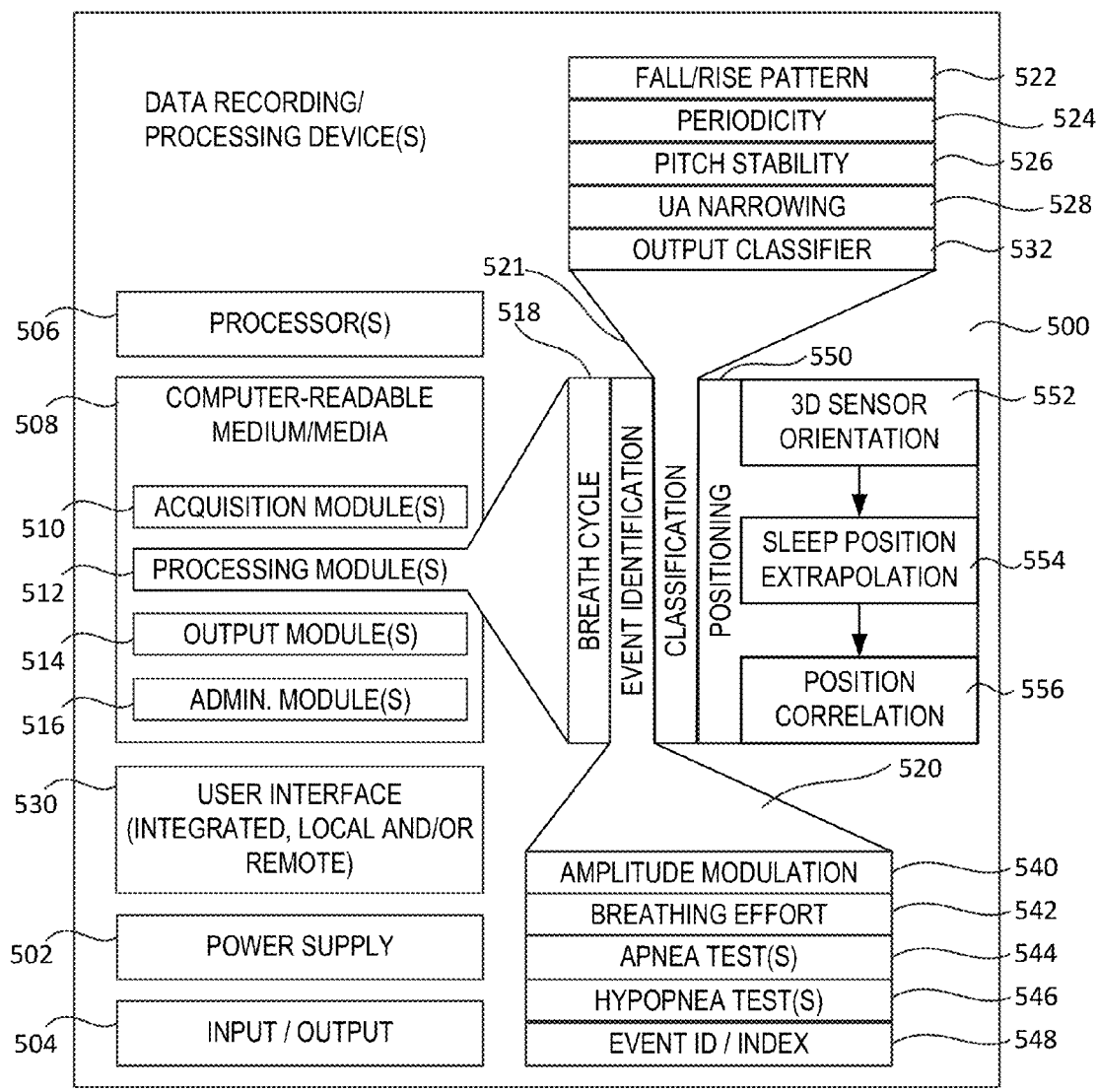
FIGS. 5A and 5B are schematic diagrams of a processing device showing exemplary complimentary processing components usable in the context of the system of FIG. 1, in accordance with one embodiment of the invention.
Figure 5B:
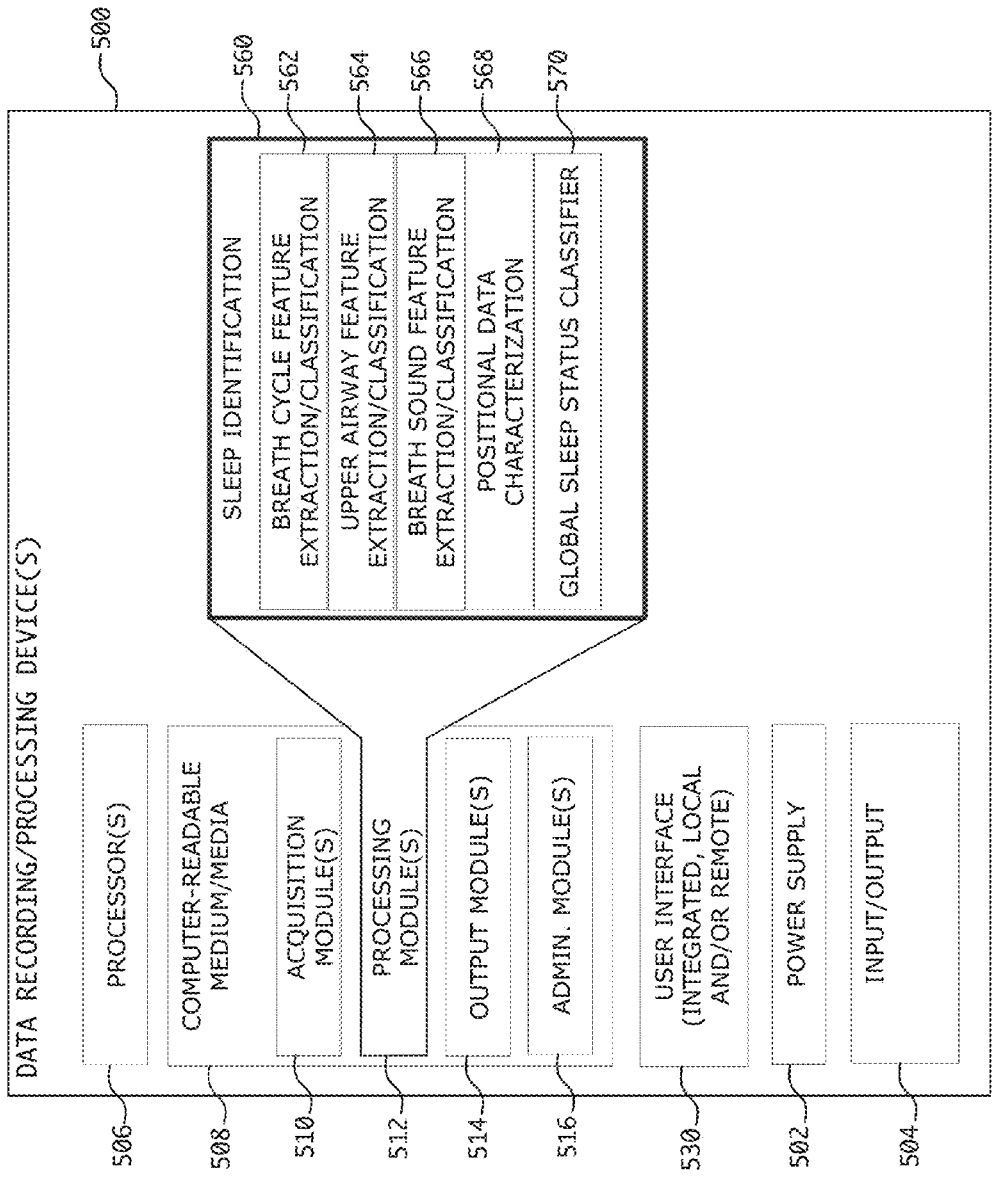

With reference to FIGS. 5A and 5B, the processing device, depicted herein generically for simplicity as a self-contained recording/processing device 500, generally comprises a power supply 502, such as a battery or other known power source, and various input/output port(s) 504 for the transfer of data, commands, instructions and the like with interactive and/or peripheral devices and/or components (not shown), such as for example, a breath monitoring mask or the like (as shown in FIGS. 1 to 4), external data processing device, display or the like. As will be appreciated by the skilled artisan, however, and as explicitly introduced above with reference to FIG. 15, the processing device may be distinct from an integrated mask recording device, whereby recorded data may be uploaded or otherwise transferred to the processing device for processing.

The device 500 further comprises one or more computer-readable media 508 having stored thereon statements and instructions, for implementation by one or more processors 506, in automatically implementing various computational tasks with respect to, for example, breath sound and positional data acquisition and/or processing. Such tasks may include, but are not limited to, the implementation of one or more breathing and/or sleeping assessment tools implemented on or in conjunction with the device 500. In the illustrative example of FIGS. 5A and 5B, these statements and instructions are represented by various processing sub-modules and/or subroutines to be called upon by the processor(s) 506 to operate the device in recording and processing breathing sounds and position in accordance with the various methods discussed below. Illustratively, the processing platform will include one or more acquisition module(s) 510 for enabling the acquisition and digitization of breath sounds generated by the candidate while breathing, as well as for the optional parallel acquisition of positional data; one or more processing module(s) 512 for processing the acquired data; one or more admin. module(s) 516 for receiving as input various processing parameters, thresholds and the like, which may be varied from time to time upon refinement and/or recalibration of the system or based on different user or candidate characteristics; and one or more output module(s) 514 configured to output process results in a useable form, either for further processing, or for immediate consumption (e.g. breath disorder identification, characterization and/or diagnosis results, indicia, position-dependence, total sleep time, number of awakenings and/or arousals, and the like). For the purpose of illustration, the processing module(s) 512 in this particular example, and with reference to the processes of FIGS. 6 and 7, discussed in greater detail below, may include, but are not limited to, a breath cycle identification module 518, e.g. to identify and/or distinguish inspiratory and expiratory breathing phases; an event identification module 520, e.g. to identify, characterize and/or count apneic and/or hypopneic events, and/or to output a value or index (e.g. apnea-hypopnea index—AHI) representative of an overall severity of the disorder; a classification module 521 for further characterizing a condition of the candidate as potentially representative of OSA vs. CSA; a positioning module 550 for processing and characterizing the position of the candidate in identifying a potential correlation between undesirable breathing events identified from processed breath sounds and candidate positioning, and/or for contributing in the evaluation of candidate sleep cycles, sleep onset, awakenings, arousals, etc.; and a sleep identification module 560

(FIG. 5B) for processing various parameters and signal characteristics in identifying candidate sleep cycles, awakenings, arousals and the like.

In this particular example, the positioning module 550 includes a 3D sensor orientation module 552 for extracting and monitoring a 3D orientation of the positional sensor from raw accelerometric data; a sleep position extrapolation module 554 for extrapolating and tracking changes in a representative position of the candidate; and a position correlation module for analyzing and identifying potential correlation(s) between candidate positioning, or changes thereof, and identified breathing events/condition(s). In one embodiment, the sleep position module may extrapolate a position of the candidate from calibrated or averaged sensor positioning data previously identified to correlate with a particular sleeping position. For example, a 3D sensor origin may be set for a horizontal head position (e.g. flat back-lying head position), and changes in position monitored in reference thereto to identify vertical (up-down) and/or lateral (side-to-side) tilt of the mask/head, which tilt values may then be correlated with observed values representative of designated sleeping positions (e.g. back-lying, front-lying, right or left side-lying, inclined head position, flat-rested head position, etc.). Different sleep position rules or parameters may be set to isolate certain sleep positions, for example based on calibrated mask orientation data, to improve accuracy and/or identify positions previously identified to be more commonly associated with known breathing disorders. For example, the mask and associated processing may be calibrated to isolate back-lying candidates whose symptoms are noticeably reduced upon positional data suggesting a change of position to a side-lying position.

It will be appreciated that different embodiments may implement different subsets and combinations of the above modules to achieve different results depending on the intended purpose of the device and/or known or suspected candidate conditions. It will be further appreciated by the skilled artisan upon reference to the following description of illustrative embodiments that each of the above-noted processing modules may itself be composed of one or more submodules for the purpose of achieving a desired output or contribution to the overall process. For example, the event identification module 520 may further comprise a breath sound amplitude modulation module 540, e.g. to extract an absolute breath sound amplitude profile; a breathing effort extraction module 542, e.g. to identify prospective events based on observed breathing effort variations; apnea/hypopnea test modules 524/526, e.g. to identify prospective events representative of true apneas/hypopneas; and an event identification module 548, e.g. to generate an event identification, overall count and/or severity index.

Similarly, the classification module 521 may be further subdivided, in accordance with one embodiment, to include a fall/rise pattern analysis module 522, e.g. to analyze breathing patterns associated with an identified event for further characterization as potentially representative of OSA vs. CSA; a periodicity identification module 524, e.g. to identify periodic sounds such as snoring; a pitch stability module 526, e.g. to further characterize identified periodic sounds as potentially representative of an obstructed airway—OSA; an upper airway (UA) narrowing detection module 528, e.g. to identify UA narrowing, which may be potentially representative of OSA, from recorded aperiodic breath sounds; and an overall classifier 532 for classifying outputs from the multiple processing modules into a singular output, as appropriate.

With particular reference to FIG. 5B, the sleep identification module 560 illustratively comprises one or more of a breath cycle feature extraction and classification module 562, for instance as described below to extract and assess a regularity of a patient's breathing; an upper airway feature extraction/classification module 564, independent from, cooperative with, or common with the UA narrowing module 528 noted above, for instance as to identify variations in upper airway narrowing/relaxation to provide some indication as to a candidate's sleep status; and a breath sound feature extraction/classification module 566 specific to the identification of sleep-specific sounds in further evaluating a candidate's sleep status. In some embodiments, the positioning module 550 may cooperate with (e.g. output to) the sleep identification module 560 in contributing to a sleep status assessment, namely in distinguishing sleep from wakefulness, or even identifying various sleep phases such as REM and NREM sleep phases. Alternatively, positional data may be independently processed by the sleep identification module 560 to achieve similar results, for example via a dedicated positional data characterization module 568. Finally, the illustrated embodiment further comprises a global sleep status classifier for assembling outputs from the various sleep identification submodules and rendering a final output for display or further processing.

As will be appreciated by the skilled artisan, while not explicitly illustrated, other processing modules may be equally subdivided into submodules consistent with preset processes to be implemented thereby, for example as described hereinbelow in accordance with different illustrative embodiments of the invention. Clearly, while the above contemplates the provision of a modular processing architecture, other process architectures may be readily applied to the present context, as will be appreciated by the person of ordinary skill in the art, without departing from the general scope and nature of the present disclosure.

The device 500 may further comprise a user interface 530, either integral thereto, or distinctly and/or remotely operated therefrom for the input of data and/or commands (e.g. keyboard, mouse, scroll pad, touch screen, push-buttons, switches, etc.) by an operator thereof, and/or for the presentation of raw, processed and/or diagnostic data with respect to breathing condition identification, characterization and/or diagnosis (e.g. graphical user interface such as CRT, LCD, LED screen or the like, visual and/or audible signals/alerts/warnings/cues, numerical displays, etc.).

As will be appreciated by those of ordinary skill in the art, additional and/or alternative components operable in conjunction and/or in parallel with the above-described illustrative embodiment of device/module 500 may be considered herein without departing from the general scope and nature of the present disclosure. It will further be appreciated that device/module 500 may equally be implemented as a distinct and dedicated device, such as a dedicated home, clinical or bedside breathing condition identification, characterization and/or diagnosis device, or again implemented by a multi-purpose device, such as a multi-purpose clinical or bedside device, or again as an application operating on a conventional computing device, such as a laptop or PC, or other personal computing devices such as a PDA, smartphone, or the like.

Furthermore, it will be appreciated that while a single all-encompassing device 500 is schematically depicted herein, various functionalities and features of the device may rather be distributed over multiple devices operatively and/or communicatively coupled to achieve a similar result. For example, in one embodiment, at least part of the functionalities of device 500 will be implemented on a local processing device integral to a self-contained breath monitoring mask, such as depicted by the embodiments of FIGS. 2 to 4. In such embodiments, the power supply, such as batteries, may be integral to the mask as well, thus providing a self-contained unit to be worn by the candidate during sleep without interference from cumbersome wires or wire harnesses. In such embodiments, the integrated processing device may be operatively coupled to the mask's one or more transducers, e.g. via one or more internal wires or a wireless link, so to provide self-contained recordal of breathing sounds during use.

The integrated device may be configured to record the raw data for subsequent transfer and processing, or may be preconfigured to implement various preprocessing and/or processing steps locally. For example, the local processing device may preprocess the recorded data in real-time to facilitate subsequent transfer, such as by digitizing the data, applying certain filters and/or amplifiers, and the like. In such embodiments, breathing sound data may be transferred in real-time, for example where the integrated device is operatively coupled to a wireless transceiver or the like, or again transferred in batches, for example, at the end of each sleep session. In the latter case, the integrated device may provide a wired or pluggable communication port for coupling to a computing device, either for immediate processing thereby, or again for communication of the recorded data to a remote processing platform (e.g. operated by a diagnostic or medical center). Alternatively, the recorded data may be stored by the integrated device on a removable medium, to be transferred to an appropriate reader for download and processing.

In other embodiments, further processing may be implemented locally on the self-contained device, with appropriate output available so to provide the user immediate access to at least some of the processed results. For example, and as will be discussed in greater detail below, preliminary results may be rendered available to the user for immediate consumption, such as an indication as to the likelihood that the candidate suffers from sleep apnea, a preliminary indication as to the severity thereof, and/or a full diagnostic of the user's condition, to name a few.

Breathing disorders are traditionally monitored and diagnosed using data acquired at sleep centers, where subjects are fitted with a number of electrodes and other potentially invasive monitoring devices, and monitored while they sleep. Clearly, as the subject is both required to sleep in a foreign setting with a number of relatively invasive and obtrusive monitoring devices attached to them, the data collected can often be misleading, if the subject even ever manages to get any sleep to produce relevant data.

Furthermore, known respiratory diagnostic systems generally require the acquisition of multiple sensory data streams to produce workable results that may include breath sounds, airflow, chest movements, esophageal pressure, heart rate, etc. Similarly, known portable monitoring devices proposed for the diagnosis of sleep apnea generally require subjects to adequately position and attach several wired electrodes responsive to a number of different biological parameters, such as listed above, which generally reduces the comfort and compliance of subjects and increases chances of detachment and/or displacement of the electrodes. Given that portable sleep apnea monitors are used in the absence of an attending health care professional, inaccurate placement or displacement of electrodes cannot be easily detected until the data is transferred to the health center.

In comparison, the provision of a portable mask for use in recording breathing sounds and positional data useable in the above-described system and below-described methods may provide a number of advantages over known techniques, including, but not limited to, patient comfort, ease of use, processing from single source data, etc.

In one exemplary embodiment, the recorded data is stored, and optionally encrypted on a removable data storage device, such as an SD card or the like. For example, analog data acquired by the one or more transducers can be locally pre-amplified, converted into digital data and stored in the removable memory device. The stored data can then either be uploaded from the memory card to a local computing device (e.g. laptop, desktop, palmtop, smartphone, etc.) for transmittal to a remotely located diagnostic center via one or more wired and/or wireless communication networks, or physically shipped or delivered to the remotely located diagnostic center for processing.

It will be appreciated that different types of data transfer and communication techniques may be implemented within the present context without departing from the general scope and nature of the present disclosure. For example, while the above example contemplates the use of a digital recording device having a removable data storage medium, such as a memory card of the like, alternative techniques may also be considered. For example, the recording device may rather include a wireless communication interface wherein data integrally recorded thereon can be wirelessly uploaded to a computing device in close proximity thereto. For example, Wi-Fi or Bluetooth applications may be leveraged in transferring the data for downstream use. Alternatively, the device may include a communication port wherein recorded data may be selectively uploaded via a removable communication cable, such as a USB cable or the like. In yet another example, the recording device itself may be removably coupled to the mask and provided with a direct communication interface, such as a USB port or the like for direct coupling to an external computing device. These and other such examples are well within the realm of the present disclosure and therefore, should not, nor should their equivalents, be considered to extend beyond the scope of the present disclosure.

Figure 6:
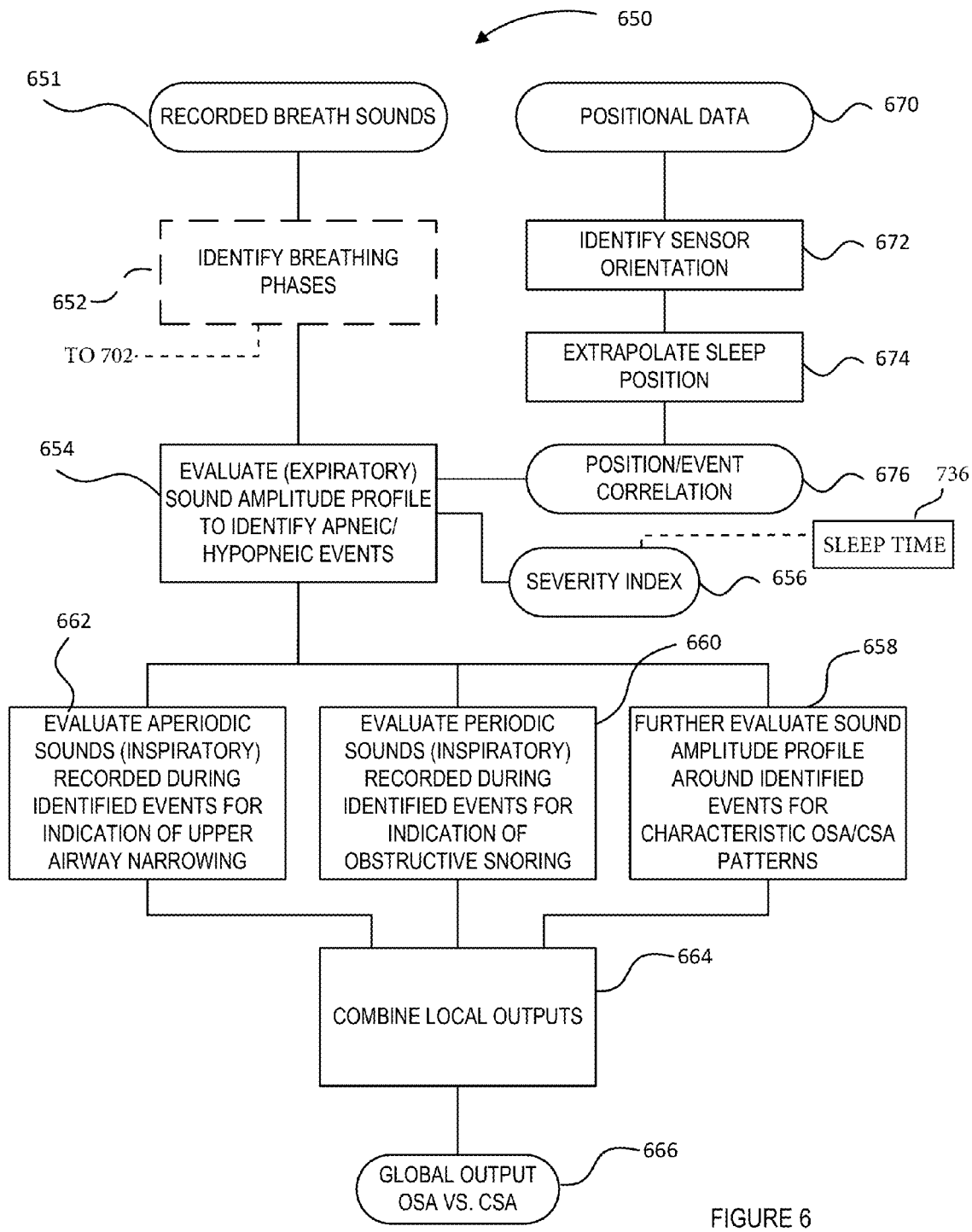
FIG. 6 is a high level flow diagram of a sleeping and/or breathing condition identification, characterization and diagnosis method, in accordance with one embodiment of the invention.

With reference to FIG. 6, and in accordance with one embodiment, a high level process 650 for identifying, characterizing and diagnosing sleep apnea will now be described. It should be noted that, while process 650 may, in accordance with one embodiment, ultimately allow for the qualification and/or quantification of a subject's breathing disorder, be it in classifying observed breathing irregularities as indicative of OSA or CSA, in outputting a value or index representative of the severity of the subject's condition, and/or in identifying a potential positional dependence of the subject' condition, the various sub-processes used in this classification may, in and of themselves, present usable results in identifying, characterizing and/or diagnosing a subject's breathing disorders, or again in providing useful general or specific breathing and/or sleeping assessments, and that, without necessarily seeking to achieve the ultimate results considered by the overall process 650. Accordingly, while the following describes an overall breath disorder identification, quantification and classification process, it will be appreciated that the scope of this disclosure should not be so limited, but rather, should be interpreted to include the various sub-process combinations that may lead, in and of themselves, to respective usable results in identifying and characterizing a subject's condition. Further details as to exemplary implementations of process 650, and the subroutines referenced therein, can be found in International Application Publication Nos. WO2012/155257 and WO2012/155251, as well as in co-pending International Application Serial No. PCT/CA2014/000009, the entire contents of which are hereby incorporated herein by reference.

In this example, breath sound data and positional data is first acquired at steps 651 and 670, respectively, via a mask having one or more transducers and a positional sensor, such as described above with reference to FIGS. 1 to 4, operatively coupled to an integral, local and/or remote recording/processing device or module for processing the recorded breath sounds and positional data, for example as described above with reference to FIG. 5A. In optional step 652, breathing cycles are identified whereby timing data associated with successive inspiratory and expiratory phases can be extracted for use in segmenting the recorded data downstream to improve processing efficiency. In the exemplary embodiment of FIG. 6 for calculating an apnea/hypopnea severity index (AHI), expiration phases, in particular, may be isolated and used to improve results. On the other hand, inspiration phase timing can be used, for example at step 662, to facilitate implementation of the exemplary upper airway narrowing detection processes described in greater detail below. Breathing cycle information may also, or alternatively be used, within the context of the breathing cycle feature extraction and classification module 562 noted above, and described in greater detail below with reference to the sleep identification process 700 depicted in FIG. 7. Namely breathing phases identified at step 652 may be used to isolate individual breathing phases at step 702, discussed below. Note that, while depicted in this example, this step is not necessarily required as other approaches may be implemented to identify data segments of interest. For example, the isolation of periodic breath sounds, which are predominantly associated with inspiration, can be automatically achieved by a frequency analysis subroutine used for further processing of such breath sound segments without prior extraction and input of breathing phase timing, as discussed in greater details in International Application Publication No. WO2012/155257.

At step 654, the amplitude profile of the digitized recording, in this embodiment focused on expiratory sound amplitudes, is automatically scanned to identify events of interest, namely events over time possibly representative of apneic or hypopneic events. Different exemplary event identification tests applicable in this context are discussed in greater detail in International Application Publication No. WO2012/155257. Upon identifying one or more such events, the data may already be classified as indicative of a subject suffering from sleep apnea. To further the characterization of the subject's condition, a severity index 656 may be calculated, for example as a function of a number of events per preset time interval, such as an Apnea-Hypopnea Index (AHI), commonly utilized in the art to characterize a severity of a subject's condition. For example, in one embodiment, identification of at least five (5) or ten (10) apneic and/or hypopneic events per hour may be characterized as representative of a candidate having at least mild apnea, whereas higher counts may be subdivided into different classes such as high or severe cases of apnea. Based on this result, a tested candidate may receive treatment or recommendations, or again be directed to further testing, screening and/or diagnostics. In one embodiment, the process 650 may take as input a total or actual sleep time 750 into consideration, such as output by the process 700 described in greater detail below with reference to FIG. 7, to output more accurate results. Alternatively, a sleep status input may be taken into consideration in identifying events of interest, for example, to assist in filtering out certain identified events that are inconsistent with a sleep status identified by the exemplary sleep status identification process 700 depicted in FIG. 7. Conversely, identified events may be used to confirm a certain sleep status indicator, for example relying on the premise that certain events such as apneas/hypopneas only occur during sleep.

Furthermore, or alternatively, the timing data of each event of interest identified at step 654 may be used for further processing to further characterize the subject's condition. For example, various tests and analyses can be implemented to independently or jointly characterize the subject's identified condition as CSA or OSA. For example, at step 658, the amplitude variation pattern of, or around an identified event can be further analyzed by the device to characterize the event as indicative of OSA or CSA. Namely, by previously identifying amplitude variation patterns typically associated with CSA and OSA, respectively, the system can be configured to automatically assess the amplitude pattern at or around a given event in comparison with such previously identified patterns to automatically classify the event as indicative of CSA or OSA. As described in greater detail in International Application Publication No. WO2012/155257, the fall rise pattern associated with an identified event can provide a reliable identifier of the subject's condition. In this particular example, for instance, gradual falling and rising edges (decrescendo/crescendo pattern) in the event amplitude profile are generally indicative of CSA, whereas a gradual fall and an abrupt rise in the event amplitude profile are generally indicative of OSA.

To increase the reliability of the system, or again to accommodate data sets or events for which amplitude profiles are not sufficiently consistent with preset patterns, complimentary tests can also be implemented by the system on the recorded breath sound data to contribute to the characterization of the subject's condition. Alternatively, these tests may be implemented in isolation to provide usable results, in accordance with some embodiments of the invention. For example, step 660 provides for the automated analysis of periodic (e.g. expiratory) sounds generated during breathing. As discussed in greater detail in International Application Publication No. WO2012/155257, relatively stable periodic sounds, e.g. those exhibiting a relatively stable pitch and/or frequency signature, may be more readily associated with CSA, whereas relatively unstable periodic sounds may be more readily associated with OSA. In this example, sound periodicity and stability analyses are generally implemented in respect of sound data acquired during and/or around identified events of interest, and in particular, with respect to inspiratory sounds. It will be understood, however, that greater data segments, or the entire data set, may be so analyzed to provide greater breadth of analysis. Namely, in one example, the entire recording may be analyzed for periodicity, and those segments so identified further processed for pitch stability. Alternatively, only periodic segments identified during and/or around identified events of interest may be considered in this step. Results as to periodic sound stability can then be used downstream, alone or in combination, to further characterize the subject's condition.

As in step 660, step 662 provides for another approach to independently or jointly participate in the characterization of the subject's condition. For example, step 662 provides for the automated analysis of aperiodic (e.g. inspiratory) sounds generated during breathing, whereby a predefined signature of such sounds can be compared to previously classified signatures in classifying these sounds as more readily indicative of OSA vs. CSA. For example, and as described in greater detail in International Application Publication No. WO2012/155257, a correlation between upper airway (UA) narrowing and aperiodic sound signatures can be defined, whereby aperiodic sounds indicative of UA narrowing may be more readily associated with OSA, as opposed to aperiodic sounds indicative of an open UA, which are more readily associated with CSA. Accordingly, upon analyzing aperiodic sound signatures in comparison with predefined signatures previously classified as a function of UA narrowing, UA narrowing during events or interest, or again during other periods within the recorded data set, may be identified and used downstream, alone or in combination, to further characterize the subject's condition.

In this example, local outputs from steps 658, 660 and 662, when applied, can be combined at step 664 to provide a global output indication 666 as to the overall result of the process 600. As discussed in greater detail in International Application Publication No. WO2012/155257, a global output may consist of an overall classification or indication as to the candidate's most likely condition (e.g. OSA or CSA) along with an indication as to a severity of the reported condition (e.g. AHI) and/or a positional dependence thereof. In other embodiments, a probability or likelihood may be associated with each condition for further interpretation or in evaluating an overall accuracy or reliability of the process in a particular case. As further detailed in International Application Publication No. WO2012/155257, different data classifiers, ranging from basic voting or weighted voting algorithms, to more complex classification systems, may be implemented to yield consistent and reliable results, depending on the intended complexity and accuracy of the intended product, for example.

As noted above, positional data 670 is acquired in this embodiment in parallel with breath sound data 651 in identifying a potential position-dependence of the candidate's condition, where applicable, and/or in contributing to the identification of sleep stages, awakenings and/or arousals during the breath sound recording. For example, raw positional data may be acquired and recorded by the device and processed to first identify an absolute or relative positional sensor orientation at step 672. For example, accelerometric data acquired by a 3D accelerometer, such as a MEMS accelerometer, may be used to identify a relative position of the sensor, and thus of the candidate wearing it, relative to a preset origin (e.g. such as a lie-flat position). From the identified sensor orientation, a sleep position of the candidate can be extrapolated at step 674, for example as introduced above in using one or more preset calibration rules, parameters or the like previously identified to associate given sensor orientation values or ranges with designated sleeping positions. At step 674, extrapolated candidate position or position changes are correlated with identified breathing events (e.g. by synchronizing timelines for each data set) in identifying potential position dependencies of the candidate's condition. Identification of such position dependencies may then be output in combination with a severity index and/or condition classification for further processing, or in guiding provision of appropriate treatment recommendations to the candidate.

As noted above, positional data 670 may also, or alternatively be used to evaluate a sleep status of the candidate, for example by correlating changes in head movement with passage through various sleep cycles and/or between sleep, awakenings and/or arousals.

Figure 7:
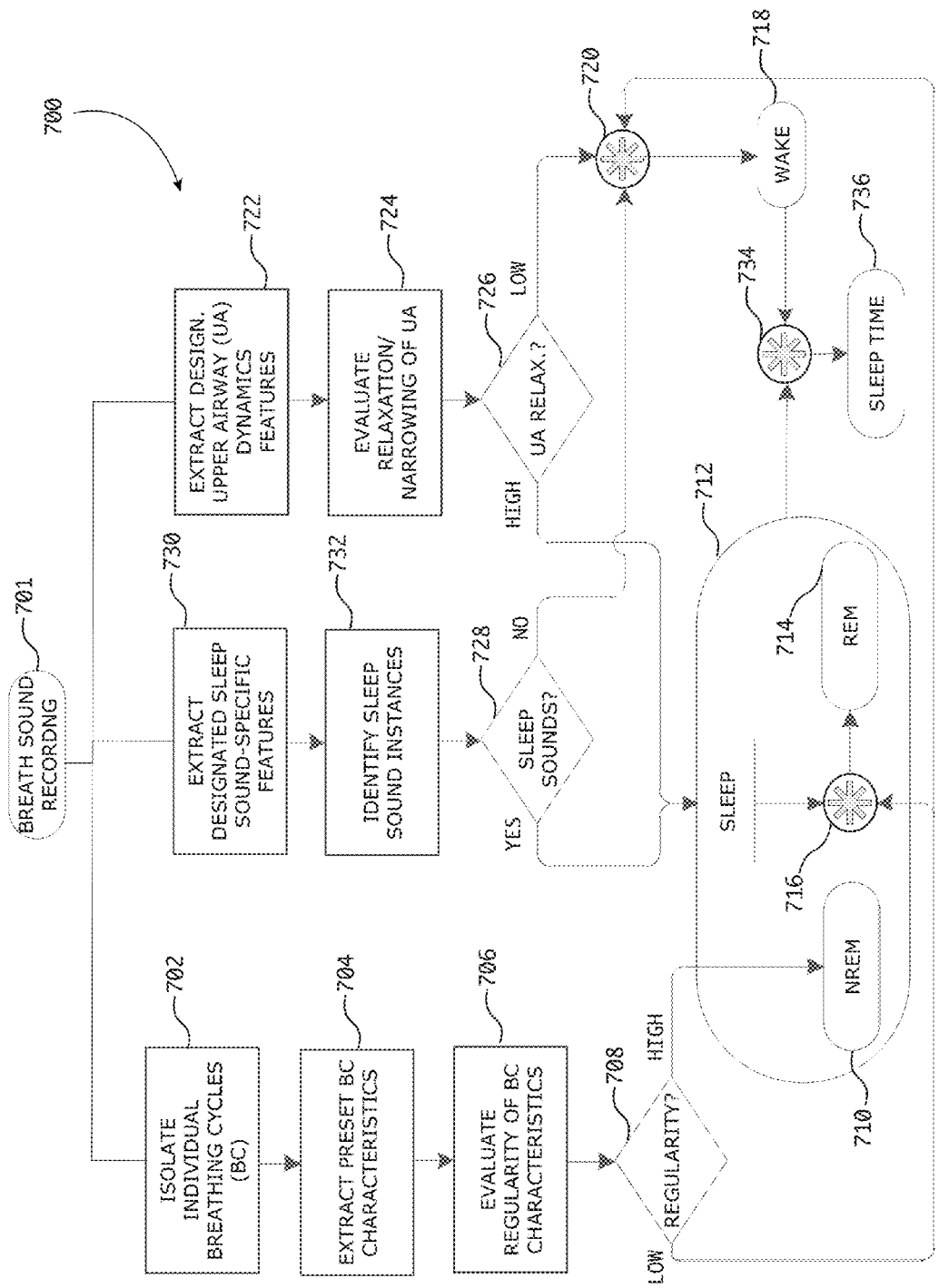
FIG. 7 is a flow diagram of an exemplary sleep detection method, in accordance with one embodiment of the invention.

With reference now to FIG. 7, and in accordance with one embodiment, a sleep status identification process, generally referred to using the numeral 700, will now be described. In this embodiment, process 700 is implemented on breath sound recordings 701 acquired via a mask having one or more transducers and an optional positional sensor, such as described above with reference to FIGS. 1 to 4, operatively coupled to an integral, local and/or remote recording/processing device or module for processing the recorded breath sounds and optional positional data, for example as described above with reference to FIGS. 5A and 5B.

At step 702, individual breathing cycles are isolated and indexed, whereby timing data associated with successive cycles can be identified in leading to the extraction of designated breathing cycle characteristic at step 704 that are evaluated for regularity at step 706, which regularity can be used, as discussed in greater detail below, to provide indication as to a current sleep status. Much as introduced above with reference to step 652 of FIG. 6, the breathing sound recording can be analyzed to automatically identify breathing phases, for example to identify timing data representative of each inspiration and expiration cycle of the subject's breathing track, which timing data can then be used, as needed, in subsequent processing steps. In this particular example, breathing cycle identification is automatically implemented by the method briefly described below and detailed in International Application Publication No. WO 2010/054481, the entire contents of which are hereby incorporated herein by reference.

Figure 8A:
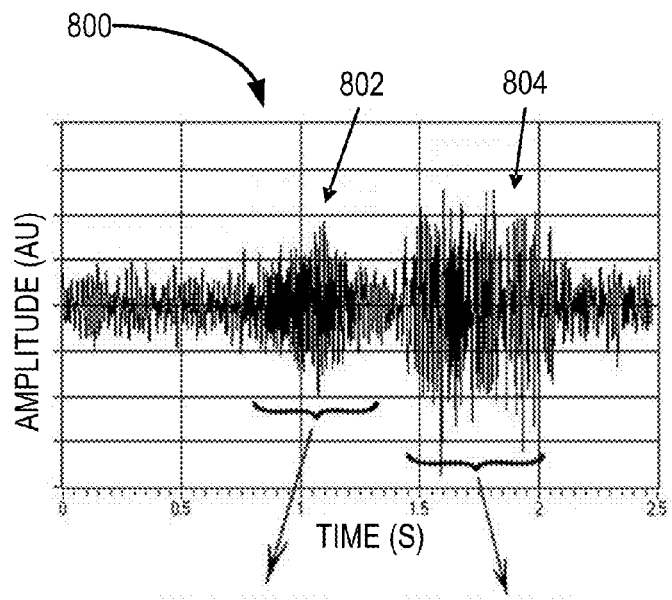
Figure 8B:
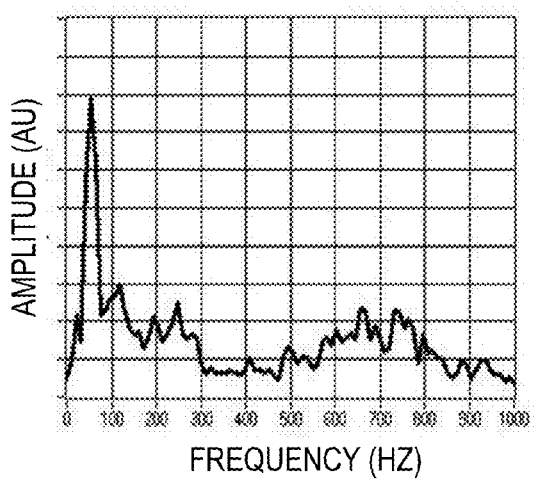
FIGS. 8B and 8C are exemplary FFT spectra for respective time segments of the inspiration phase and expiration phase of FIG. 8A, in accordance with one embodiment of the invention.
Figure 8C:
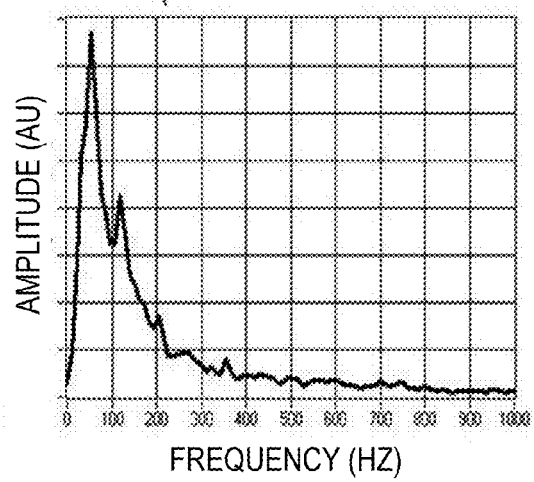

Briefly, an acoustic data waveform plot, for example as shown in the waveform versus time plot 800 of FIG. 8A for a single breath showing both an inspiration phase 802 and an expiration phase 804, can be processed using this method to automatically extract therefrom an indication as to each inspiratory and expiratory breathing cycle. In particular, a spectral analysis of the acoustic data, for example as shown by the exemplary FFT spectra of FIGS. 8B and 8C for respective time segments of the inspiration phase 802 and expiration phase 804 of FIG. 8A, can be used to achieve this result. As can be seen in FIG. 8B in respect of the inspiration phase, a sharp narrow band of harmonics is identified below 200 Hz and another peak is again identified above 400 Hz. Comparatively, the expiratory spectrum, as shown in FIG. 8C, forms a wider band that spans frequencies up to 500 Hz whose power drops off rapidly above this frequency.

Using this observed distinction between spectral compositions for inspiration and expiration data, appropriate frequency-domain metrics can be formulated to automatically distinguish the two types of phases. For example, in this particular embodiment, the bands ratio (BR) of summed frequency magnitudes between 400 to 1000 Hz, to frequency magnitudes between 10 and 400 Hz can be calculated for successive time segments of the recorded data to automatically identify inspiratory and expiratory phases, where higher BR values represent inspiration phases as compared to expiration phases. The following equation provides an exemplary approach to calculating the BR for a given time segment:

$$BR = \sum_{400\,Hz}^{1000\,Hz} FFT(f) \Big/ \sum_{10\,Hz}^{400\,Hz} FFT(f)$$

where the numerator represents the sum of FFT higher frequency magnitude bins which lie between 400 and 1000 Hz, and the denominator represents the sum of FFT lower frequency magnitude bins which lie between 10 and 400 Hz, for example. Upon setting appropriate BR values for inspiration and expiration cycles, determined generally or with respect to a particular subject or class of subjects, automated breathing cycle identification can be implemented.

The person of ordinary skill in the art will appreciate that while the above describes one example of an automated approach to breathing cycle identification via breath sound analysis, other techniques, not necessarily limited to breathing sound analyses, may also be considered herein to achieve a similar effect, and that, without departing from the general scope and nature of the present disclosure. For example, other automated techniques achieved via the capture and processing of complimentary data, such as via Respiratory Inductance Plethysmography (RIP), (Respitrace Ambulatory Monitoring Inc., White Plains, N.Y., USA), which provides thoracoabdominal displacement data representative of changes of tidal volume during respiration, can also or alternatively be used to compliment further processing. Alternatively, visual identification of breathing phases may be implemented by a trained technician, albeit at the expense of some system automation. In yet another embodiment, inspiratory and expiratory phases may be identified via the breathing sound classification method described below, which may be used to automatically distinguish recorded breath sounds associated with inspiration from those associated with expiration.

Once breathing cycles have been identified, and in accordance with one embodiment, a regularity of certain characteristics/features thereof can be examined in providing indication as to sleep status. For example, as shown below, respiratory depth (tidal volume) and frequency (respiratory rate) become more regular with less breath-to-breath variations during NREM sleep than during wakefulness and REM sleep, and can thus be used to provide a first characteristic in isolating sleep stages and/or statuses (e.g. isolating NREM sleep).

As illustrated generally in FIG. 7, individual breaths or breathing cycles (i.e. each consisting of an inspiratory and expiratory component) are first isolated at step 702. For the sake of the below example, detected expirations were used as a marker for defining individual breaths, and were detected via the bands ratio technique noted above. Each breathing cycle is then assigned a certain reference point or cycle index, which may be selected as, but is not limited to, the beginning, middle, or end of each expiration, the beginning, middle, or end of each inspiration, the beginning, middle, or end of each snore (where snoring is detected, e.g. as per the approach discussed in greater detail below), the mid-point between inspiration and expiration, etc.

At step 704, one or more breathing cycle (BC) characteristics/features are extracted for consideration. In this example, these features include those extracted from calculated inter-breath intervals (IBI), which characteristic is defined as the time interval between 2 successive cycles as determined by the cycle index; and those extracted from calculated inter-breath cycle energies (IBCE), where the cycle energy (CE) is defined as the breath sound signal energy (such as inspiration, expiration, or snoring) and is proportional to the tidal volume.

As demonstrated below, IBI and CE become more regular during NREM sleep than during wakefulness and REM sleep. Accordingly, at step 706, a relative regularity of the extracted features is evaluated. For example, a relative measure of the IBI and IBCE entropy, variance and dispersion can, when taken alone or in combination, and as demonstrated below, yield useable results in outputting indication as to sleep status. In the example depicted in FIG. 7, where a regularity of certain breathing cycles or segments is automatically determined at step 708 to be relatively high, the process 700 automatically assigns an NREM sleep status 710 to these cycles/segments; otherwise, the process considers secondary measures in determining whether these cycles/segments should be assigned a general sleep status 712 and thus in this case a REM status 714 via digital logic block 716, or a wake status 718, as described in further detail below. In other embodiments, extracted features may be further trained to isolate each status specifically without secondary input, whereas in yet other embodiments, each status may only be reliably designated upon secondary confirmation from one or more additional classification streams via one or more designated digital logic blocks.

In support of the above-described process, a first experiment took data from 14 subjects that each underwent overnight polysomnography (PSG) with simultaneous breath sound recordings acquired via a mask, such as that described above with reference to FIGS. 1 to 4. Sleep status for the whole overnight recording was identified using electroencephalography (EEG), submental electromyography (EMG) and electro-oculography (EOG), which is a part of a standard PSG. Breath sound segments (S) of at least 10 minutes duration were isolated from both wakefulness and NREM sleep from each of the 14 subjects. A total of 60 segments from NREM sleep and 39 from wakefulness were isolated. The average duration of segments was 18 and 29 minutes for NREM sleep and wakefulness, respectively. Given that the respiratory rate was 10-20 breathes per minute, each segment had at least 100 breaths.

To calculate regularity of breathing, in accordance with one embodiment, the IBI was first determined for each S and the following measures were calculated, where d(i) is the inter-breath interval in seconds between breaths i and i+1, N is the number of IBIs in each frame, s is the shift between frames, j is the frame index, and where $p_j(x)$ is the probability of observing an IBI of duration x in frame j.

$$\text{Mean: } \mu_j = \frac{1}{N} \sum_{i=1+sj}^{N+sj} d(i)$$

$$\text{Variance: } \sigma_j^2 = \frac{1}{N-1} \sum_{i=1+sj}^{N+sj} (d(i) - \mu_j)^2$$

$$\text{Index of Dispersion: } D_j = \frac{\sigma_j^2}{\mu_j}$$

$$\text{Kurtosis} = \frac{\frac{1}{N} \sum_{i=1+sj}^{N+sj} (d(i) - \mu_j)^4}{\left(\frac{1}{N} \sum_{i=1+sj}^{N+sj} (d(i) - \mu_j)^2\right)^2}$$

$$\text{Skewness} = \frac{\frac{1}{N} \sum_{i=1+sj}^{N+sj} (d(i) - \mu_j)^3}{\left(\frac{1}{N} \sum_{i=1+sj}^{N+sj} (d(i) - \mu_j)^2\right)^{3/2}}$$

$$\text{Entropy: } H(j) = \int_0^\infty p_j(x) \log(p_j(x)) \, dx$$

Also tested was the approximate entropy, which is a measure of the unpredictability of a time-series signal; it is calculated by first embedding the time-series data into vectors and computing a similarity metric between all possible combinations of vectors.

In this example, the regularity measures were calculated on windows of 100 breaths at a time, with a 10-breath shift. In total, this gave 2705 data points from the 14 subjects in this example. The results are tabulated in table 1, below, where p<0.05 for differences between NREM and Wake, and between NREM and REM statues, with the exception of Kurtosis values which were not significantly different between REM and NREM statuses.

TABLE 1

Extracted IBI Feature Values for Each Class of Interest

|  | Sleep | NREM | REM | Wakefulness |
|---|---|---|---|---|
| Shannon (Continuous) Entropy | 3.40 | 3.26 | 3.79 | 3.84 |
| Index of Dispersion | 1.12 | 0.94 | 3.07 | 3.73 |
| kurtosis | 8.05 | 7.60 | 8.96 | 10.52 |
| Approximate Entropy | 0.08 | 0.05 | 0.15 | 0.21 |
| Skewness | 0.54 | 0.41 | 1.16 | 1.65 |
| Variance | 91.12 | 65.54 | 203.73 | 293.52 |

From these results, one clearly observes that all feature measures for NREM sleep are lower than those for REM sleep and wakefulness indicating less variability and more regularity of IBI and, therefore, more regular breathing. In these results, the class 'Sleep' is a combination of both REM and NREM sleep class, where all measures of regularity are again lower in sleep than wakefulness. FIGS. 9A to 9E present bar charts of selected features to further illustrate differences observed between these classes. This thus serves to validate the use of recorded breath sounds, as considered herein, for tracking breathing regularity to automatically output indication of sleep status.

Figure 10:
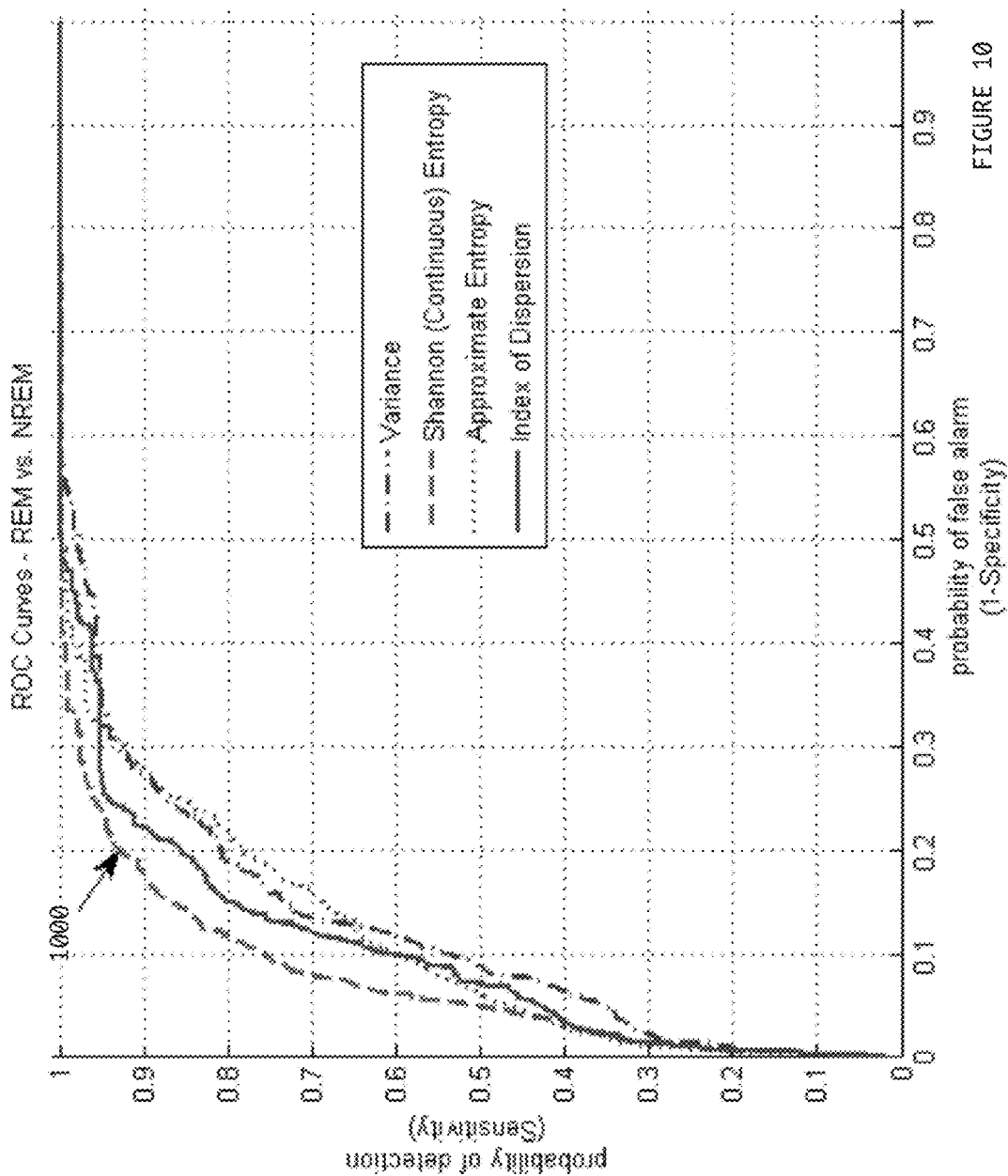
FIGS. 10 to 12 are receiver operating characteristic curves (ROC) for selected IBI regularity features in identifying REM vs. NREM, Sleep vs. Wake, and wake vs. NREM statuses, respectively, in accordance with on embodiment of the invention.
Figure 11:
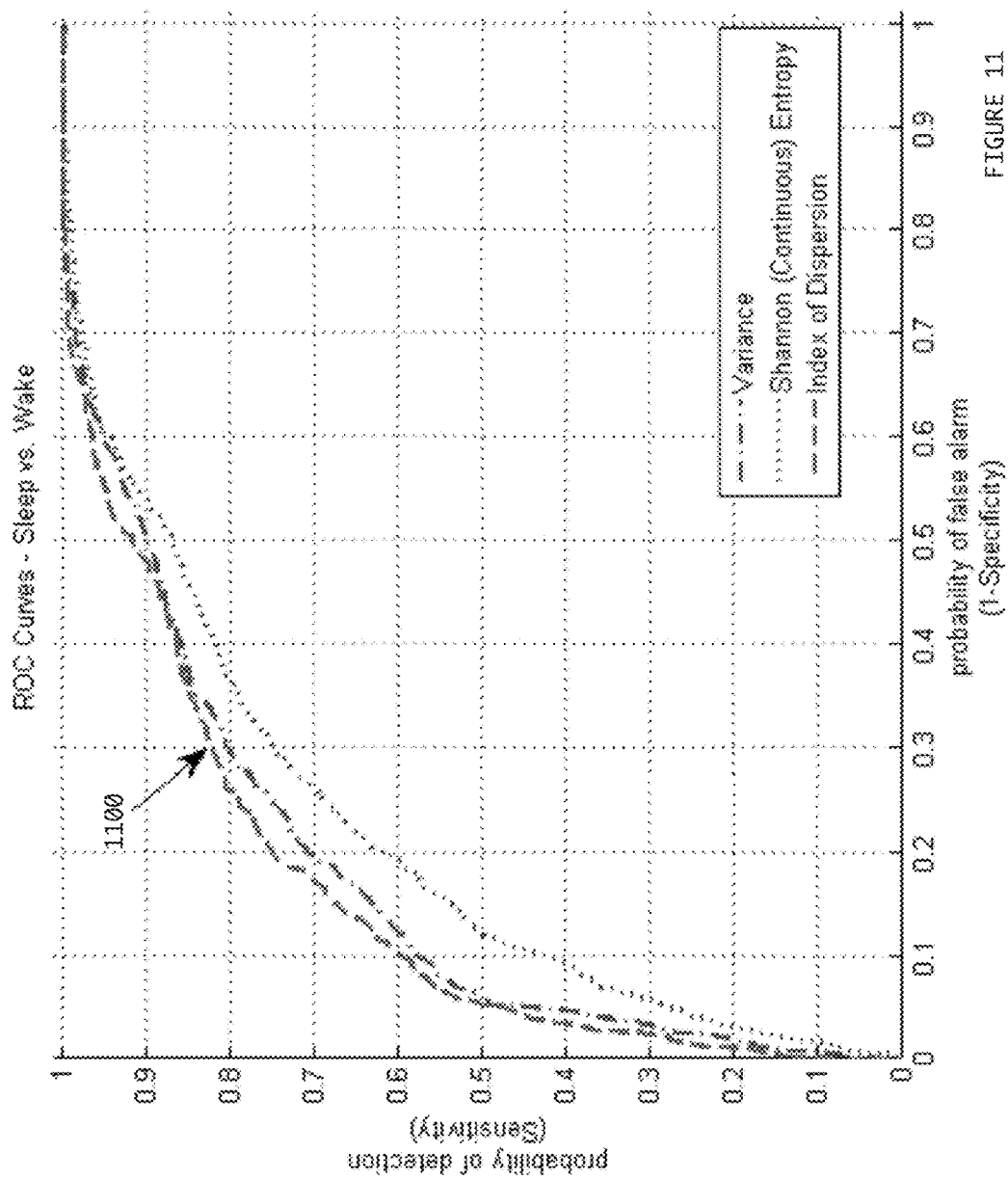
Figure 12:
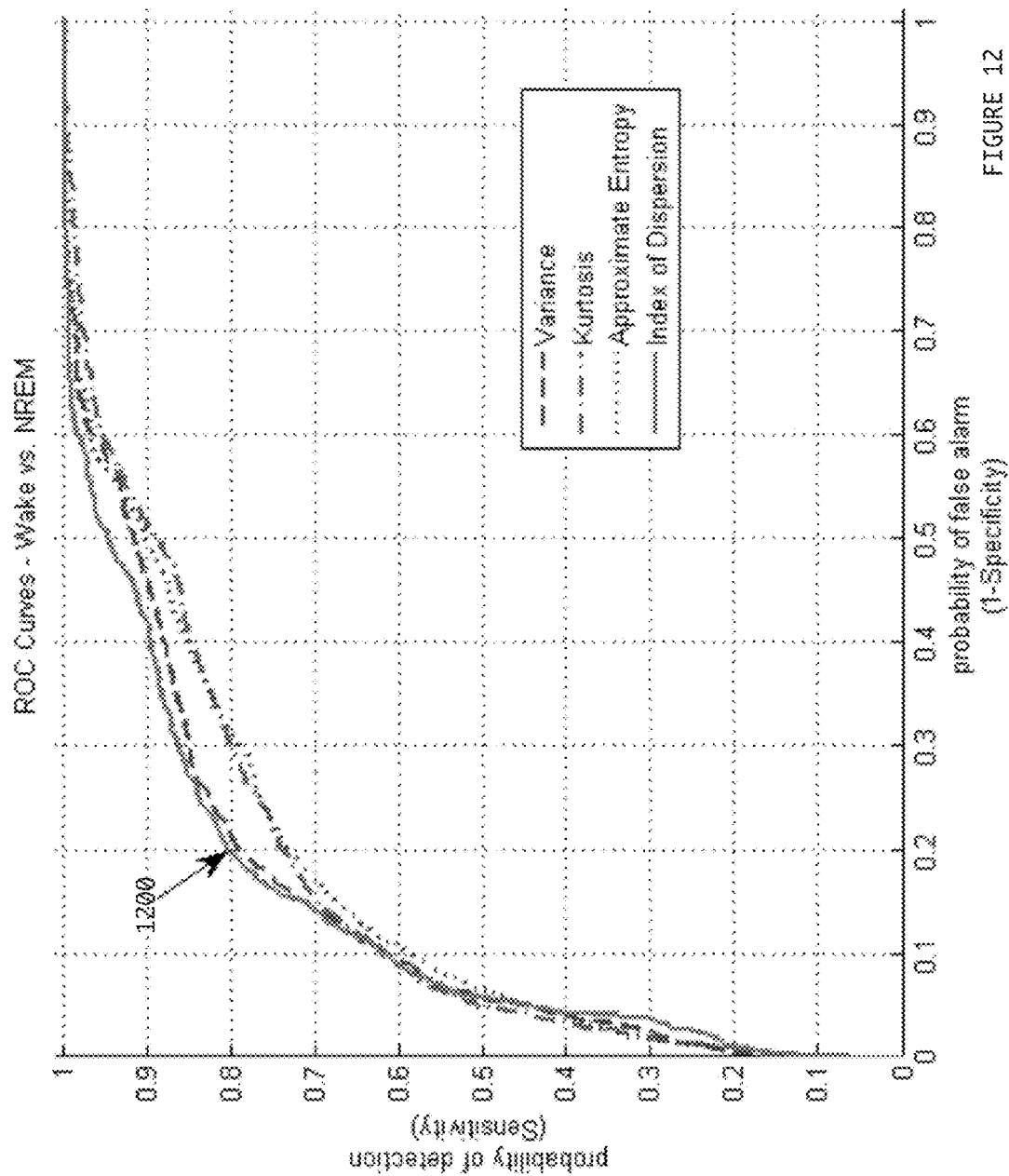

The receiver operating characteristic curves (ROC) for selected regularity features were also calculated, as shown in FIGS. 10 to 12 for REM vs. NREM, Sleep vs. Wake, and wake vs. NREM, respectively, to indicate the ability to differentiate sleep and wake statues from the recorded breath sounds. The higher the area under the curve (AUC), the better the feature is at segregating classes of interest. The AUC for the different features are tabulated below.

TABLE 2

ROC curve AUC Values for Each Extracted IBI Features

|  | Shannon (Continuous) Entropy | Index of Dispersion | Kurtosis | Approximate Entropy | Skewness | Variance |
|---|---|---|---|---|---|---|
| NREM vs. Wake | 0.85 | 0.87 | 0.71 | 0.85 | 0.77 | 0.86 |
| NREM vs. REM | 0.92 | 0.89 | 0.54 | 0.88 | 0.71 | 0.87 |

As seen in FIG. 10, for example, by setting a certain threshold 1000 for the extracted IBI-Shannon (continuous) entropy feature, a sensitivity of approximately 90% sensitivity and a specificity of approximately 80% can be reached in distinguishing NREM sleep (more regular) from REM sleep (less regular).

As similarly shown in FIGS. 11 and 12, by setting respective thresholds 1100 and 1200 for the extracted IBI-Index of Dispersion feature, sleep and wake statuses can be distinguished with 80% sensitivity and 70% specificity, whereas wake and NREM statuses can be distinguished with 80% sensitivity and 80% specificity, respectively.

In a second experiment, CE was used instead of IBI for evaluating BC regularity, whereby CE is used as a surrogate for tidal volume. The difference between 2 successive CE is herein referred to as inter-breath cycle energy (IBCE). The same techniques to calculate the regularity of IBCE were used as that described above with respect to IBI. The extracted feature values are listed below in Table 3, where p<0.05 for differences between NREM and Wake, and NREM and REM statuses, except for Kurtosis and skewness values which were not significantly different between any of the statuses.

TABLE 3

Extracted IBCE Feature Values for Each Class of Interest

|  | NREM | REM | Wake |
|---|---|---|---|
| Shannon (Continuous) Entropy | 0.14 | 0.57 | 0.86 |
| Index of Dispersion | 0.54 | 0.88 | 1.15 |
| Kurtosis | 10.16 | 10.02 | 10.31 |
| Approximate Entropy | 0.02 | 0.07 | 0.14 |
| Skewness | 2.09 | 2.24 | 2.23 |
| Variance | 0.32 | 0.80 | 1.52 |

As with IBI, the extraction and evaluation of designated IBCE features can be clearly shown to lead to an observable distinction between NREM and REM, as well as between NREM and Wake statuses.

Figures 13A, 13B:
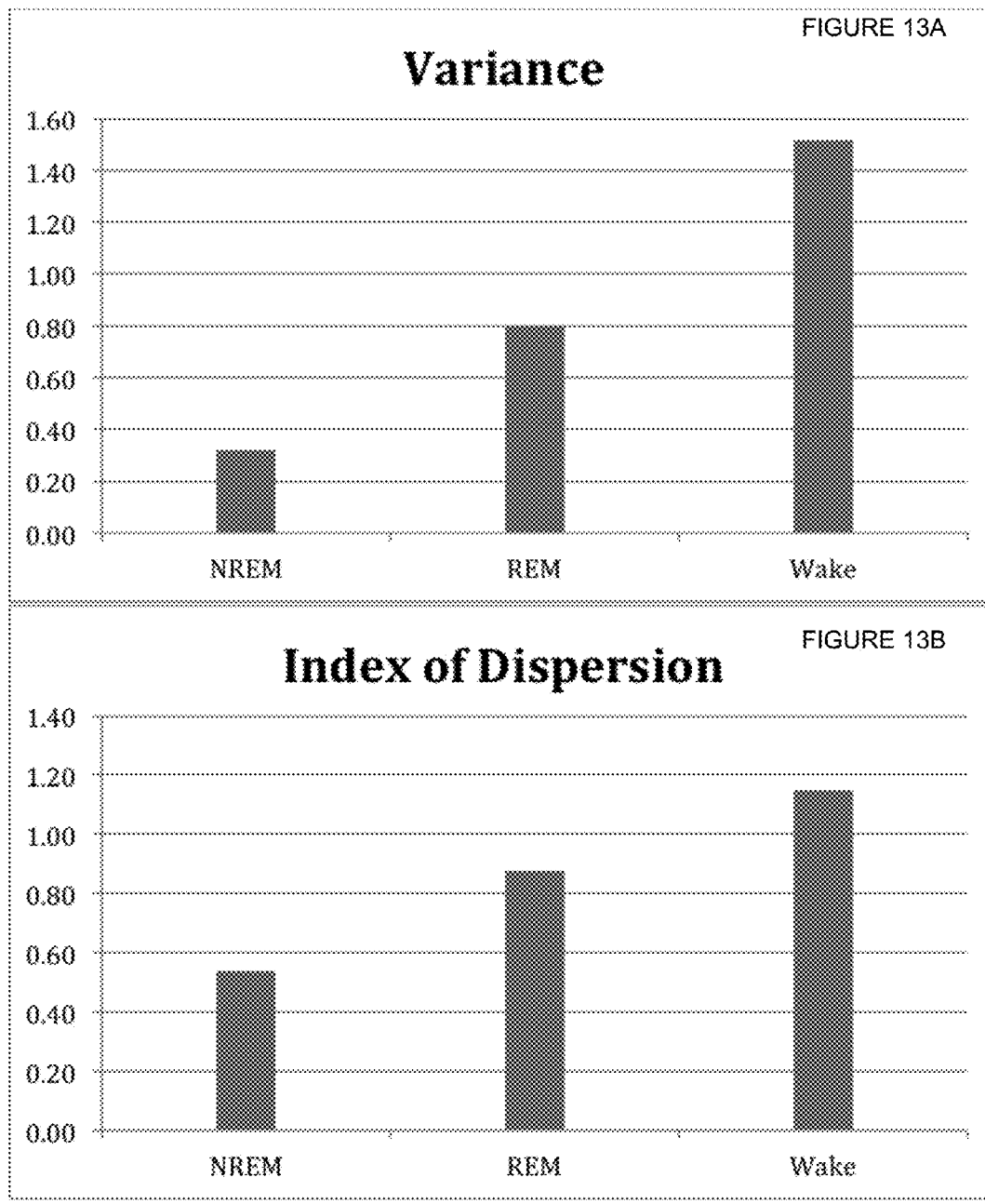
FIGS. 13A and B are bar charts of selected features extracted from recorded breath sounds to automatically distinguish between sleep statuses based on inter-breath cycle energy (IBCE) regularity, in accordance with one embodiment of the invention.

FIGS. 13A and 13B present bar charts of selected features to further illustrate differences observed between these classes. This thus serves to further validate the use of recorded breath sounds for tracking breathing regularity, this time via extracted IBCE features, to automatically output indication of sleep status.

It will be appreciated that while the above independently contemplates the use of IBI and IBCE features extracted from recorded breath sounds, these and other breathing cycle characteristics may also considered, alone or in combination, to achieve useable results, and that, without departing from the general scope and nature of the present disclosure. For instance, different IBI, IBCE and/or other extracted features can be used separately or in various combinations, such as provided for example, but not limited to, via linear, non-linear, or weighted combinations.

With reference again to FIG. 7, and in accordance with one embodiment, secondary and/or alternative measures may also be invoked from the recorded breath sounds 701 to either independently arrive at a sleep status indication (i.e. general sleep or awake statuses 712 and 718, respectively) or contribute to a global status indication via one or more combinatory digital logic blocks, such as digital logic blocks 716 and 720.

For instance, in one embodiment, the method 700 further processes the acquired breath sound data to output indication as to a relative relaxation of the subject's upper airway, which relaxation during sleep contributes to an increase in air turbulence. The upper airway muscle tone drops immediately after the onset of sleep. This continues throughout the course of sleep and includes all sleep stages and is generally independent of snoring. Therefore, extracting a relative measure of upper airway relaxation from recorded breath sounds can provide a complimentary or independent sleep status indicator, whereby a relaxed and thereby narrowed upper airway indicates that the subject is likely asleep, as compared to evaluating from recorded breath sounds that the upper airway is relatively open and thus that the subject is more likely to be awake.

For instance, turbulence generally changes the acoustic nature of sounds, which can be inferred from several sound features such as its spectral peaks, spectral tilt, spectral flatness, linear predictive coefficients (LPC) and also non-spectral features such fractals, to name a few.

As previously discussed in International Application Publication No. WO2012/155257, LPC coefficients have been shown to provide a good indicator for upper airway narrowing (i.e. relaxation) within the context of OSA/CSA diagnosis. LPC coefficients are thus used in the present context to evaluate upper airway narrowing for distinguishing sleep from wakefulness. In accordance with one embodiment, recorded breath sounds at 701 are processed to extract therefrom at step 722 designated features, such as provided via LPC, that are then evaluated/compared at step 724 to provide a relative indicator as to upper airway narrowing/relaxation. Where evaluated features are classified at step 726 as being indicative of a relatively high relaxation/narrowing, the local process outputs a general sleep status 712. Alternatively, the local process outputs a general wake status 718, which in this embodiment, is combined with an output of the regularity evaluator 708 to distinguish between wake 718 and REM 714 statuses.

To train the classifier 726, one approach may include, but is not limited to the following example.

Breath sound data is first collected from overnight sleeping subjects using a device such as that described above with reference to FIGS. 1 to 4. The acquired data is then segmented into segments (S) 5 to 10 minutes long and that are known to correspond to both sleep and wake statues as confirmed by EEG. Since inspirations are generally associated with increased negative pressure and more turbulence, in one embodiment, the data segments S are each processed to identify inspiratory phases, for example as described above with reference to FIG. 8A to 8C. It will be appreciated that expiratory phases or full breathing cycles may alternatively be used to achieve similar results without departing from the general scope of the present disclosure.

LPC coefficients can then be extracted from each inspiration (and/or expiration in some embodiments) corresponding to sleep and wakefulness, and a classifier trained on these extracted features to cluster LPC coefficients as belonging to sleep (with narrower airway and therefore more turbulence) and wakefulness (with more open airway and therefore less turbulence). Once trained, the classifier can then be used to classify new sound recordings and output a sleep status indication (i.e. sleep vs. wake).

Within the context of FIG. 7, new sound recordings 701 would first be processed to isolate inspiratory phases, and then segmented for processing via LPC in which extracted LPC coefficients designated during the training process would be automatically classified by the trained classifier as being indicative of sleep vs. wakefulness. Alternatively, one or more preset thresholds may be established with known data during the training phase to automatically classify LPC coefficients extracted from newly acquired sound recordings.

Using this method, a correlation between upper airway (UA) narrowing/relaxation and aperiodic sound signatures can be made using Linear Prediction Coding (LPC), which relies on similarities identified between aperiodic breathing sounds and the generation of unvoiced fricative sounds in speech production. In each case, the quality or signature of sounds generated can be recognized to vary according to the degree of narrowing. Using this analogy, the methods and devices herein described allow, based on breath sound analysis, for the objective detection of UA narrowing/relaxation occurrences, which detected occurrences can then be used, in accordance with some embodiments, in sleep status identification. For example, in one embodiment, variations are detected in pure turbulent breath sound qualities in correlation with a change of a quantitative index of UA narrowing, thus leading to an objective determination of relative UA narrowing/relaxation.

In this particular example, aperiodic breath sound signatures can be developed and correlated with an UA narrowing index to classify recorded breath sounds based on a level of UA narrowing. For the purpose of process 700, it will be appreciated that different levels of UA narrowing identification may lead to different degrees of accuracy; however, a binary system whereby segments associated with significant UA narrowing (e.g. above a certain classification threshold) are distinguished from those with little to no UA narrowing, may be sufficient in contributing to the overall classification process.

As will be appreciated, various supervised and unsupervised pattern recognition algorithms such as k-mean, fuzzy c-means, artificial neural networks, support vector machines, and Hidden Markov Models, may be used to provide useable results. Since LPC is a frequency spectrum based technique that represents the frequency spectrum in smooth curves with emphasis on peaks, techniques other than LPC may also be considered to provide a like effect, such as by leveraging characteristics of FFT and mel-frequency cepstrum coefficients (MFCC), for example.

As shown above, LPC and its equivalents can be used, in accordance with some embodiments, to characterize turbulent (aperiodic) breath sounds as indicative of sleep or wakefulness, which may be used alone or in combination with other methods to output a general or specific sleep status output.

Again with reference to FIG. 7, as sleep induces relaxation of upper airway muscles, which relaxation may result in the production of distinct aperiodic sounds as discussed above, it may also result in the production of period sounds generally known as snoring. Snoring is one example of a type of sound that can take place in any sleep stage, i.e. both in REM and NREM sleep, and therefore, can be used as a feature for distinguishing sleep from wakefulness.

Within the present context, a method has thus been developed to accurately identify snoring instances from recorded breath sounds, which identified instances can then be used to contribute to identifying a sleep status. However, the below-described method is not limited as such, as it can also be used to isolate a number of distinct breath sounds not limited to snoring, which can thus yield interesting and complimentary results to that shown in FIG. 7.

For instance, and in accordance with some aspects of the herein-described embodiments, a breath sound component classification system and method can be deployed to automatically concurrently classify multiple breath sound components, which may include, but are not limited to, inspiration, expiration, inspiratory snoring, expiratory snoring, wheezing, other noise, non-audible, and combinations thereof. For example, in some embodiments, breathing phases and snoring phases may be concurrently or jointly identified to automatically segregate inspiration-based and expiration-based snoring components to provide further characterization of the tested candidates' breathing conditions. Namely, breathing phases identified according to this approach may also be used in other subprocesses, for example in the context of UA narrowing/relaxation that is, in some embodiments, constrained to inspiratory breath sound segments.

Furthermore, in some embodiments, techniques described herein may be employed to establish a subject-independent platform. For instance, a subject independent method for automatic classification of breath and related sounds during sleep is described in detail below, in accordance with an exemplary embodiment.

In this particular example, an experienced operator manually labeled segments of breath sounds from 11 sleeping subjects as: inspiration, expiration, inspiratory snoring, expiratory snoring, wheezing, other noise, and non-audible. Ten features were extracted and fed into 3 different classifiers: Naïve Bayes, Support Vector Machine, and Random Forest. A leave-one-out method was used in which data from each subject, in turn, were evaluated using models trained with all other subjects. Mean accuracy for concurrent classification of all 7 classes reached 85.4%. Mean accuracy for separating data into 2 classes, snoring (inspiration only) and non-snoring, reached 97.8%. These accuracies clearly demonstrate the power and commercial utility of the herein disclosed techniques, providing, in some embodiments, a subject-independent solution to automated breath sound component classification and analysis, be it for the concurrent isolation of all breath sound components and/or for the isolation of snoring (e.g. inspiration-based snoring only) from all other breath sound components.

In this example, breath sounds were recorded from 11 subjects during overnight sleep using an electret microphone in front of the face embedded in a small open mask at a sampling rate of 16 kHz. Five minute segments (L) were extracted from the first, middle, and last third of the overnight recording of each subject. A total of 33 segments, yielding 165 minutes of data, were extracted. An experienced annotator listened to each segment and manually identified each sound unit as one of: inspiration, expiration, snoring, wheezing, not-audible, and other-noise. Wheezing is a high pitch musical sound. Although it can rarely be detected at the upper airway level, it was given a separate class for completeness. Snoring is typically an inspiratory phenomenon, yet expiratory snoring can also take place in rare cases, in which case it should have distinct acoustic characteristics. Therefore, a separate class for expiratory snoring was created to yield a total of 7 classes. For simplicity, the mere term 'snoring' herein will refer to inspiratory snoring alone since it represents the majority of snoring episodes.

Each L was segmented using a moving window of 64 ms with 50% overlap, herein referred to as (W). From each W, the following 10 features were extracted.

Periodicity:
An autocorrelation-based algorithm known as the robust algorithm for pitch tracking (RAPT) was applied to sampled breath sounds. RAPT calculates the periodicity of W as a value between 0 and 1, denoting total randomness and complete periodicity respectively.

Frequency Bands Ratio:
As expiration has most of its energy concentrated in the frequency band below 400 Hz and vice versa for inspiration, a ratio of frequency bin magnitudes below 400 Hz to those above 400 Hz was calculated to extract this feature from sampled breath sounds.

Spectral Centroid:
This feature indicates the 'center of spectral mass', which is perceptually related to the 'brightness' of a sound and is given by:

$$\frac{\sum_{n=0}^{N-1} f(n)x(n)}{\sum_{n=0}^{N-1} x(n)}$$

where x(n) represents the magnitude of bin number n, and f(n) represents the center frequency of that bin.

Flatness:
This feature indicates whether the spectral distribution is smooth or spiky, and results from the ratio between its geometric and arithmetic means, given by:

$$\text{Flatness} = \frac{\sqrt[N]{\prod_{n=0}^{N-1} x(n)}}{\frac{\sum_{n=0}^{N-1} x(n)}{N}}$$

where x(n) represents the magnitude of bin number n.

Shannon Entropy:
This is a measure of uncertainty of a random variable X given by:

$$H(x) := -\frac{\sum_{i=1}^{n} p(x_i)\log_b p(x_i)}{\log(\text{length}(p))}$$

where $p(x_i)$ is the probability mass function of X.

Zero Crossing Rate:
This feature is the number of zero crossings (both positive and negative) present in the segment normalized by the length of the segment.

Uniformity:
This feature measures the uniformity of the negative peak amplitudes of a windowed segment. The peaks are obtained by estimating the local maxima and minima. The uniformity value is then defined by:

$$U = \frac{std(\text{peak}_{neg})}{\text{mean}(\text{peak}_{neg})}$$

where $\text{peak}_{neg}$ are peaks following negative zero crossings.

Shimmer:
Shimmer is a time domain feature used in speech processing that is quantified as:

$$\text{Shimmer} = \frac{\sum_{i=1}^{N-1} |X(n) - X(n+1)|}{N-1}$$

where X is obtained by a 3rd-order median filtering of W.

Click Factor:
Clicks are defined as the sharp loud peaks resulting from tissue collision as happens with snoring, whether periodic or non-periodic. Clicks manifest as transient wide frequency bands in the spectrogram, analogous to a step function. To identify this pattern, a pre-emphasis filter is applied to spectra of W and short-time spectrograms are obtained (window size=256 points [16 ms] with 75% overlap). The frequency bins are then summed, which converts the spectrogram from a 2 dimensional to a 1 dimensional waveform. The latter is then de-trended to remove local offsets and the resulting waveform is herein defined as K. The roughness of K reflects the occurrence of sharp transients in the time domain (clicks). The click factor is quantified as: C=mean $((10 \times K)^2)$.

Relative Energy:

The ratio of the root mean square of W to the positive maximum signed 16 bit integer level was defined as the 'relative energy' level for a given segment. This is an expression of a signal's energy as a proportion of its allowed maximum amplitude.

As will be appreciated by the skilled artisan, other features may be considered herein, as well as different subsets and combinations thereof, to produce similar effects, and that, without departing from the general scope and nature of the present disclosure.

Three classification methods are compared in this example: Naïve Bayes (NB), support vector machine with sequential minimal optimization (SVM), and random forest (RF). These three methods differ greatly in the optimization of the parameters, with both the SVM and RF models optimizing (separate) discriminative criteria. The Naïve Bayes classifier assumes conditional independence between its features. The SVM is a parametric classifier that provides highly non-linear decision boundaries given particular kernels; a polynomial kernel of degree 2 is used herein. RF is an ensemble classifier that returns the mode of the class predictions across several decision trees. In this example, the RF used the standard Breiman algorithm with 5 trees. Parameters for the SVM kernel and RF were set empirically.

As will be appreciated by the skilled artisan, other classification methods may be considered herein, as well as different subsets and combinations thereof, to produce similar effects, and that, without departing from the general scope and nature of the present disclosure.

In order to ensure generality of the trained models, a leave-one-subject-out cross validation method (LOSOCV) was implemented. Using LOSOCV, all subject data sets except one were used for training, which is used for validation to obtain the accuracy of identifying sound classes in that 1 subject. The process is then repeated in such a way that each subject is used for validation exactly once. The total accuracy is averaged over individual scores. This approach tends to preclude effects of over-fitting to the training data. This was done twice—once for the 7-way classification of the classes described above and once for the binary classification of snoring versus all other sounds. Snoring was selected from among the other classes as an exemplary class given its clinical relevance. Yet, any one of the other classes, such as inspiration or expiration etc., can be equally chosen depending on the intended application.

Figure 14:
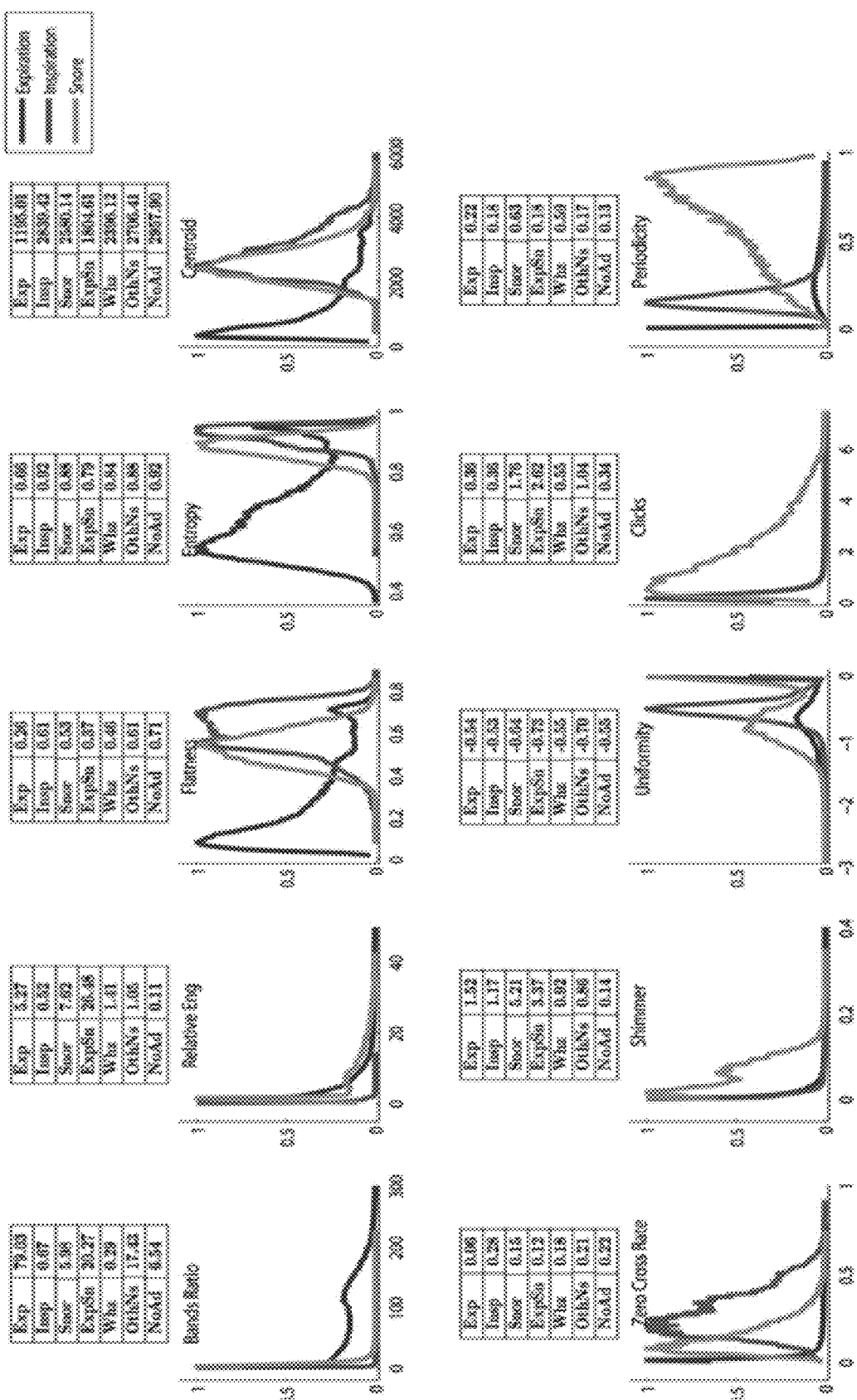
FIG. 14 is a group graphical distributions (histograms) for 10 features extracted in the automatic classification of recorded breath sounds, in accordance with one exemplary embodiment, across 3 main identified sound classes: expiration, inspiration, and snoring; each illustrated distribution is further accompanied by its feature mean values for 7 sound classes identified in this exemplary embodiment, annotated as follows: Expiration (Exp), Inspiration (Insp), Snoring (Snor), Expiratory Snoring (ExpSn), Wheezing (Whz), Other Noise (OthNs), Not Audible (NoAd); each distribution curve was normalized to unity to facilitate visualization.

The mean values for the 10 acoustic features and their distributions for 3 of the 7 classes are displayed in FIG. 14. Accuracies across classifiers and participants are shown in Table 4, below. The mean accuracy for distinguishing the 7 classes concurrently ranged between 79.7% with NB and 85.40% with SVM. On the other hand, when the problem was reduced to a 2-class problem (snoring vs. not-snoring), performance improved remarkably to between 94.9% with NB and 97.8% with RF. The discriminative classifiers outperformed NB, but the unprecedented high accuracy of the latter may indicate that the selected features are indeed highly informative to the identification of snores.

As noted above, individual components of breath sounds can be identified using the herein described techniques with a high degree of accuracy, and using a totally subject-independent scheme. Accuracy for identifying all breath and related sounds reached 85.4% in the 7-class problem and 97.8% in the binary identification of snores. Validation was performed using a LOSOCV scheme, which shows that these results can be duplicated in practical situations in which a trained system can be used to classify breath sounds in new subjects.

Furthermore, the herein described techniques allows for the concurrent classification of all selected breath sounds including snoring (inspiratory and expiratory), inspiration, expiration, wheezing, in addition to non-respiratory noises.

Accordingly, non-snoring breath sounds may also be identified and segregated to advantage, which may carry important information about the upper airway dynamics of the subject at hand. For example, as noted above, the upper airway is prone to narrowing and collapse during inspiration more than expiration, due to the negative lung pressure. Both expiratory and inspiratory phases can be used for accurate tracking of breathing rate and activities. At least for these reasons, the detection and concurrent isolation of various breathing sound components can provide a useful tool in research and clinical settings.

As noted above, a group of features were selected to characterize the physical nature of breath sounds. FIG. 14 displays the distribution of the 10 features across the most common breath sounds. Periodicity for example was highest in snoring. Periodicity arises with snoring due to collision of tissue pliable flaps of the upper airway, in contrast to the other sounds that are turbulent in nature. The click factor was also highest in snoring since it captures sharp tissue collisions regardless of periodicity. On the other hand, expiration is characterized by concentration of spectral energy in the lower bands, which resulted in remarkably lower spectral centroid values than other classes. Relative energy was lowest in the 'not audible' class.

Table 4 reports on differences in performance across subjects. Subject P1, for example, had an especially low accuracy across all classifiers. The data of this subject contained atypically numerous instances of the class 'expiratory snoring', which is not a commonly occurring sound. Larger sets of representative training data could be used to improve the robustness of the above-described example. Regardless, significant accuracies were demonstrated to produce usable results in the classification of breath sound components, and ultimately, in the analysis and possible diagnosis and/or treatment of breathing conditions/disorders. Namely, the results of presented herein demonstrate that the techniques considered provide a comprehensive yet practical and pragmatic classification model that takes in consideration all breath sounds and achieves high performance in new unseen subject data.

TABLE 4

Average and Median Accuracy Achieved by LOSOCV for the 11 Subjects

| Classifier | P1 | P2 | P3 | P4 | P5 | P6 | P7 | P8 | P9 | P10 | P11 | Avg | Med | Std |
|---|---|---|---|---|---|---|---|---|---|---|---|---|---|---|
| 7-Class Classification Problem, Snoring vs. Non-Snoring | | | | | | | | | | | | | | |
| NB | 52.2 | 76.2 | 90.3 | 65.2 | 88.9 | 80.3 | 84.1 | 87.9 | 89.3 | 75.6 | 86.6 | 79.7 | 84.1 | 11.9 |
| SVM | 67.7 | 86.5 | 91.1 | 70.7 | 93.1 | 86.5 | 89.5 | 91.3 | 86.1 | 84.8 | 91.5 | 85.4 | 86.5 | 8.44 |
| RF | 56.4 | 87.1 | 84.3 | 74.6 | 91.4 | 87.8 | 88.7 | 92.1 | 86.6 | 85.6 | 89.6 | 84.0 | 87.1 | 10.3 |
| 2-Class Classification Problem | | | | | | | | | | | | | | |
| NB | 88.0 | 94.7 | 98.0 | 94.0 | 99.1 | 97.5 | 92.4 | 99.5 | 95.5 | 88.2 | 97.0 | 94.9 | 95.5 | 4.0 |
| SVM | 92.1 | 97.2 | 97.7 | 93.8 | 99.8 | 97.9 | 97.9 | 99.8 | 91.4 | 94.5 | 99.6 | 96.5 | 97.7 | 3.0 |
| RF | 85.0 | 98.3 | 94.2 | 97.3 | 99.9 | 98.5 | 97.8 | 100.0 | 94.7 | 97.1 | 99.8 | 97.8 | 98.0 | 2.0 |

P1 . . . 11: Patients 1 to 11;
Avg: Average;
Med: Median;
Std: Standard Deviation;
NB: Naive Bayes;
SVM: Support Vector Machines;
RF: Random Forests Based on the above, and within the context of FIG. 7, a relatively accurate identification of snoring instances can be achieved, which, in combination with other techniques described herein, allows for a robust sleep identification method that can, in some embodiments, further serve to distinguish not only between sleep and wake statuses, but also between different sleep stages such as NREM and REM.

For example, the process 700 is generally limited to a binary sleep sound-specific classification setting in that the process seeks only to distinguish sounds generated during sleep (e.g. snoring) from those generated during the wake state. Much like the UA relaxation branch of the process 700, the sleep sound-specific branch relies on a trained or thresholding classifier 728 to classify designated sleep sound-specific features extracted at step 730 and identified at step 732 to distinguish sleep-related sounds, such as snoring, from wake-related sounds. As a result, the local classifier 728 will output one of a general sleep status indicator 712 and wake status indicator 718, which, when correlated with other process outputs via digital logical blocks 716 and 720, may further distinguish recorded breath sounds into identifying any one of wake (718), REM (714) and NREM (710) states.

As will be appreciated by the skilled artisan, different process logics may be applied to the various outputs to yield accurate results. For example, in the illustrated process 700 of FIG. 7, a high regularity output is sufficient to trigger the NREM indicator 710, whereas the REM indicator 714 is only triggered upon sleep status confirmation from at least one of two secondary sleep status indicators. Depending on the relative accuracy of each classifier, and possibly as a function of a reliability measure integral to each one thereof built into the classification model (e.g. confidence level output), some classification outputs may be assigned a higher weight than others in allowing for greater certainty in output accuracy, or again in dealing with conflicting results. For example, a weak upper airway relaxation classification may yield an output that is more likely indicative of the wake status, but that may be trumped by a highly accurate classification of low breath cycle regularity to ultimately output a global NREM indicator. These and other permutations are therefore intended to fall with the scope of the present disclosure.

Furthermore, other techniques for contributing to a distinction between sleep and wake statuses may be considered, as appropriate depending on the subject at hand. For example, and as briefly discussed above, the positive identification of apneic and hypopneic events, as considered in greater detail in International Application No. WO 2012/155257, may also be used to confirm a general sleep status, for example, in the absence of a positive or reliable identification of snoring and/or UA relaxation. Similarly, sleep mask movements identified from acquired positional data may also be correlated with different sleep or wake statuses.

Finally, and again with reference to FIG. 7, upon classifying a given breath sound recording, for example taken overnight or during a designated sleep period, the time segments associated with a confirmed sleep status can be cumulated via logical block 734 to output an overall sleep time 736, for example usable in the context of process 600 shown in FIG. 6 to output a more accurate severity (e.g. AHI) index.

While the present disclosure describes various exemplary embodiments, the disclosure is not so limited. To the contrary, the disclosure is intended to cover various modifications and equivalent arrangements included within the general scope of the present disclosure.

What is claimed is:

1. A computer-implemented method, automatically implemented by one or more processors of a computing device, for automatically characterizing digitized breath sounds recorded from a subject over time as indicative of the subject being one of asleep and awake to accurately assess a potential sleep disorder of the candidate, the method comprising:
   identifying, by the one or more processors, individual breathing cycles in a given segment of said recorded breath sounds;
   calculating, by the one or more processors, one or more preset breathing cycle characteristics from said identified breathing cycles;
   evaluating, by the one or more processors, a relative regularity of said calculated preset breathing cycle characteristics for said given segment; and
   upon said relative regularity satisfying a preset high regularity condition, outputting, by the one or more processors, a sleep status indicator indicating that the subject was likely asleep during said segment;
   otherwise or upon said relative regularity satisfying a preset low regularity condition, outputting, by the one or more processors, a wake status indicator indicating that the subject was likely awake during said segment; and compiling, by the one or more processors, each said wake status indicator or said sleep status indicator for each said given segment to compute and output an actual sleep time to be associated with said breath sound recording during which the subject is asleep in accurately assessing the potential sleep disorder of the candidate.

2. The computer-implemented method of claim 1, wherein said sleep status indicator comprises a NREM sleep indicator or a REM sleep indicator, wherein said preset high regularity condition encompasses two distinct high regularity conditions, and wherein satisfying a higher one of said two distinct high regularity conditions triggers said NREM sleep indicator whereas satisfying a lower one of said two distinct high regularity conditions triggers said REM sleep indicator.

3. The computer-implemented method of claim 1, wherein said one or more preset breathing cycle characteristics comprise at least one of an inter-breath interval and an inter-breath cycle energy.

4. The computer-implemented method of claim 3, further comprising extracting one or more designated features from said one or more preset breathing cycle characteristics, and wherein said evaluating step comprises evaluating said regularity as a function of said extracted one or more designated features.

5. The computer-implemented method of claim 4, wherein said extracted one or more designated features comprise at least one of entropy, dispersion or variance.

6. The computer-implemented method of claim 1, wherein the method further comprises automatically determining a severity of the potential disorder by automatically identifying and compiling a number of sleep disorder events from said breath sound recording and computing a severity index therefor as a function of said number and said actual sleep time.

7. The computer-implemented method of claim 6, wherein the potential disorder comprises sleep apnea and wherein said severity index comprises an apnea-hypopnea index (AHI).

8. A computer-implemented method, automatically implemented by one or more processors of a computing device, for automatically characterizing digitized breath sounds recorded from a subject over time as indicative of one of a sleep status or a wake status to accurately assess a potential sleep disorder of the candidate, the method comprising:

identifying, by the one or more processors, individual breathing cycles in a given segment of said recorded breath sounds;

calculating, by the one or more processors, a relative regularity of said identified breathing cycles;

comparing, by the one or more processors, said relative regularity with one or more preset regularity conditions to output at least one of a high regularity and a low regularity indicator indicative of the sleep status and the wake status, respectively, for said given segment; and confirming, by the one or more processors, in response to said high regularity indicator, the wake status indicated by said high regularity indicator for said given segment, by at least one of:

identifying an instance of snoring during said given segment by extracting one or more designated snore-related features from said recorded breath sounds in said given segment previously determined to distinguish snoring sounds from non-snoring sounds; or identifying an instance of relatively high upper airway relaxation during said given segment by extracting one or more designated upper airway relaxation-related features from said recorded breath sounds in said given segment previously determined to distinguish relatively high upper airway narrowing instances from relatively low upper airway narrowing instances; and compiling, by the one or more processors, each said wake status or said sleep status for each said given segment to compute an actual sleep time to be associated with said breath sound recording during which the subject is asleep in accurately assessing the potential sleep disorder of the candidate.

9. The computer-implemented method of claim 8, wherein said sleep status comprises either of a NREM sleep status and a REM sleep status, wherein said one or more preset regularity conditions encompasse two distinct high regularity conditions, and wherein satisfying a higher one of said two distinct high regularity conditions triggers said NREM sleep status whereas satisfying a lower one of said two distinct high regularity conditions triggers said REM sleep status.

10. The computer-implemented method of claim 9, wherein said NREM sleep status is output irrespective of whether either of said instance of relatively high upper airway narrowing and said instance of snoring is identified.

11. The computer-implemented method of claim 9, wherein said REM sleep status is output only upon the sleep status being confirmed by said instance of relatively high upper airway narrowing and/or said instance of snoring being identified.

12. The computer-implemented method of claim 8, wherein the method further comprises automatically determining a severity of the potential disorder by automatically identifying and compiling a number of sleep disorder events from said breath sound recording and computing a severity index therefor as a function of said number and said actual sleep time.

13. The computer-implemented method of claim 12, wherein the potential disorder comprises sleep apnea and wherein said severity index comprises an apnea-hypopnea index (AHI).

* * * * *